US006936432B2

(12) United States Patent
Gopalan et al.

(10) Patent No.: US 6,936,432 B2
(45) Date of Patent: Aug. 30, 2005

(54) BACTERIAL RNASE P PROTEINS AND THEIR USE IN IDENTIFYING ANTIBACTERIAL COMPOUNDS

(75) Inventors: Venkat Gopalan, Columbus, OH (US); Milan Jovanovic, Dublin, OH (US); Paul S. Eder, Oreland, PA (US); Tony Giordano, Phoenixville, PA (US); Gordon D. Powers, Malvern, PA (US); K. Asish Xavier, West Chester, PA (US)

(73) Assignee: Message Pharmaceuticals, Malvern, PA (US)

( * ) Notice: Subject to any disclaimer, the term of this patent is extended or adjusted under 35 U.S.C. 154(b) by 29 days.

(21) Appl. No.: 09/798,635

(22) Filed: Mar. 1, 2001

(65) Prior Publication Data

US 2004/0127480 A1 Jul. 1, 2004

Related U.S. Application Data

(63) Continuation-in-part of application No. 09/516,061, filed on Mar. 1, 2000.

(51) Int. Cl.$^7$ .............................. C12N 9/22; C12Q 1/34
(52) U.S. Cl. ......................................... 435/18; 435/199
(58) Field of Search .................................. 435/199, 18

(56) References Cited

FOREIGN PATENT DOCUMENTS

| WO | EP 0 811 688 A | 12/1997 |
|---|---|---|
| WO | WO 98 18931 A | 5/1998 |
| WO | WO 99 11653 A | 3/1999 |

OTHER PUBLICATIONS

Spitzfaden, C., et al. (2000) J. Mol. Biol. 295, 105–115.*
Mikkelsen, N.E., et al. (1999) Proc. Natl. Acad. Sci., USA 96, 6155–6160.*
Alm et al., Genomic–sequence comparison of two unrelated isolates of the human gastric pathogen *Helicobacter pylori*. Nature 397:176–180 (1999).
Andersen et al., Identification of a region of genetic variability among *Bacillus anthracis* strains and related species. J. Bacteriol. 178:377–84 (1996).
Andersson, et al. The genome sequence of *Rickettsia prowazekii* and the origin of mitochondria. Nature 396 (6706):133–140 (1998).
Blattner et al., The complete genome sequence of *Escherichia coli* K–12. Science 277:1453–1474 (1997).
Clark et al., Sequence Analysis of a 34.7–kb DNA Segment from the Genome of *Buchnera aphidicola* (Endosymbiont of Aphids) Containing groEL, dnaA, the atp operon, gidA and rho. Curr. Microbiol 36(3):158–163 (1998).
Cole et al., Deciphering the biology of *Mycobacterium tuberculosis* from the complete genome sequence. Nature 393:537–544 (1998).

Ferretti et al., Complete genome sequence of an M1 strain of *Streptococcus pyogenes*. Proc Natl Acad Sci USA 98:4658–63 (2001).
Fleischmann et al., Whole–genome random sequencing and assembly of *Haemophilus Influenae* Rd. Science 269:496–512 (1995).
Fraser et al, The minimal gene complement of *Mycoplasma genitalium*. Science 270:397–403 (1995).
Fraser et al., Genomic sequence of a Lyme disease spirochaete, *Borelia burgdorferi*. Nature 390:580–586 (1997).
Fraser, et al., Complete genome sequence of *Treponema pallidum*, the Syphilis Spirochete. Science 281:375–388 (1998).
Fsihi et al., Gene arrangement and organization in a ~76kb fragment encompassing the orlC region of the chromosome of *Mycobacterium leprae*. Microbiology 142:3147–3161 (1996).
Fujita et al., Structure of the dnaA region of *Micrococcus luteus*: conservation and variations among eubacteria. Gene 93(1):73–78 (1990).
Glass et al., The complete sequence of the mucosal pathogen *Ureaplasma urealyticum*, Nature 407:757–762 (2000).
Glass et al., The *Ureaplasma urealyticum* Genome project, American Society for Microbiology Meeting on *E. coli* and small genomes, Utah, Oct. 1997.
Heidelberg et al., DNA sequence of both chromosomes of the cholera pathogen *Vibrio cholerae*. Nature 406:477–83 (2000).
Himmelreich et al., Complete sequence analysis of the genome of the bacterium *Mycoplasma pneumoniae*. Nucl. Acids Res. 24(22):4420–4449 (1996).
Kalman et al., Comparative genomes of *Chlamydia pneumoniae* and *C. trachomatis*. Nat. Genet. 21(4):385–389 (1999).
Kunst et al., The complete genome sequence of the Gram–positive bacterium *Bacillus subtilis*. Nature 390:249–256 (1997).
Miyata et al, Mapping of replication initiation site in *Mycoplasma capricolum* genome by two–dimensional gel–electrophoretic analysis. Nucl. Acids Res. 21(20):4816–4823 (1993).
Morse and Schmidt, Sequences encoding the protein and RNA components of ribonuclease P from *Streptomyces bikiniesis var zorbonensis*. Gene 117(1):61–66 (1992).
Nelson et al., Evidence for lateral gene transfer between Archaea and Bacteria from genome sequence of *Thermotoga maritima*. Nature 399(6734):323–329 (1999).
Ogasawara et al., Genes and their organization in the replication origin region of the bacterial chromosome. Mol. Microbiol. 6(5):629–634 (1992).

(Continued)

Primary Examiner—Charles L. Patterson, Jr.
(74) Attorney, Agent, or Firm—Clark & Elbing LLP; Kristina Bieker-Brady

(57) ABSTRACT

The invention features novel RNase P molecules and nucleic acids encoding the same. Methods for discovery of antimicrobial compounds are also featured.

15 Claims, 20 Drawing Sheets

OTHER PUBLICATIONS

Parkhill et al., Complete DNA sequence of a serogroup A strain of *Neisseria meningitidis* Z2491. Nature 404:502–6 (2000).

Parkhill et al., The genome sequence of the food–borne pathogen *Campylobacter jejuni* reveals hypervariable sequences. Nature 403:665–8 (2000).

Pasqual and Vioque, Cloning, purification and chatacterization of the protein subunit of ribonuclease P from the cyanobacterium *Synechocystis* sp. PCC 6803. Eur. J. Biochem. 241(1):17–24 (1996).

Read et al., Genome sequence of *Chlamydia trachomatis* MoPn and *Chlamydia pneumoniae* AR39, Nucleic Acids Research 28(6):1397–1406 (2000).

Redenbach et al., A set of ordered cosmids and a detailed genetic and physical map for the 8Mb *Streptomyces coelicolor* A3(2) chromosome. Mol. Microbiol. 21(1):77–96 (1996).

Region from a *Bordetella pertussis*. Tohama I sequence from Sanger center & MDS Contig 267. Accession No. NC_002928, Jul. 5, 2002.

Region from a *Bordetella pertussis* sequence. Accession No. NC_002929, Nov. 6, 2001.

Region from a *Burkholderia pseudomallei* sequence. Accession No. NC_002930, Feb. 22, 2001.

Region from a *Chlamydia muridarum* sequence. Accession No. AE 002284, May 16, 2000.

Region from a *Chlamydophila psittaci* sequence. 2003.

Region from a *Clostridium difficile* 630 (epidemic type X) sequence from Sanger center Contig 975. Accession No. NC_002933, Nov. 6, 2001.

Region from a *Corynebacterium diptheriae* sequence from Sanger center Contig. 390. Accession No. NC_002935, Nov. 6, 2001.

Region from a *Enterococcus faecalis* V583 sequence. Apr. 22, 2003.

Region from a *Haemophilus ducreyi* sequence. Accession No. NC_002940, Oct. 24, 2001.

Region from a *Kiebsiella pneumoniae* M6H 78578 sequence from Washington University Contig 632. Accession No. NC_002941, Jul. 7, 1999.

Region from a *Legionella pneumophila* sequence. Accession No. NC_002942, Oct. 15, 2001.

Region from a *Mycobacterium avium* 104 sequence from TIGR. Accession No. NC_002943, Feb. 14, 2002.

Region from a *Mycobacterium smegmatis* sequence. Accession No. NC_002974, Feb. 14, 2002.

Region from a *Neisseria gonorrhoea* FA 1090 sequence from University of Oklahoma ACGT Contig. 60. Accession No. NC_002946, Sep. 28, 2000.

Region from a *Pasteurella multocida* PM70 sequence. Accession No. AE 004439, Nov. 25, 2002.

Region from a *Porphyromonas gingivalis* W83 sequence from TIGR & Forsyth Dental Center. Accession No. NC_002950, Dec. 7, 2001.

Region from a *Staphylococcus epidermidis* sequence. Accession No. AE15929, Jan. 2, 2003.

Region from a *Salmonella paratyphi* A ATCC 9150 sequence from Washington University. Accession No. NC_002963, Jul. 7, 1999.

Region from a *Staphylococcus aureus* COL sequence from TIGR. Accession No. NC_002951, Sep. 14, 2001.

Region from a *Staphylcoccus aureus* NCTC sequence from University of Oklahoma ACGT Config. 561, Accession No. NC_002954, Dec. 4, 2001.

Region from a *Streptococcus mutans* UAB159 sequence from University of Oklahoma ACGT Contig. 299. Accession No. NC_002956, Dec. 14, 2001.

Region from a *Treponema denticola* sequence. Accession No. NC_002967, Feb. 14, 2002.

Skovgaard, Nucleotide sequence of a *Proteus mirabilis* DNA Fragment homologous to the 60K–mpA–rpmH–d–naA–dnaN–recF–gryB Region of *Escherichia coli*. Gene 93(1):27–34 (1990).

Stephens et al., Genome sequence of an obligate intracellular pathogen of humans: *Chlamydia trachomatis*. Science 282:754–9 (1998).

Stover et al., Complete genome sequence of *Pseudomonas aeruginosa* PAO1, an opportunistic pathogen. Nature 406:959–64 (2000).

Suhan et al., Cloning and characterization of an autonomous replication sequence from *Coxiella burnetii*. J. Bact. 176(17):5233–5243 (1994).

Takami et al., Replication origin region of the chromosome of alkaliphilic *Bacillus halodurans* C–125. Biosci. Biotechnol. Biochem. 63(6):1134–1137 (1999).

Tettelin et al., Complete genome sequence of a virulent isolate of *Streptococcus pneumoniae*. Science 293:498–506 (2001).

Tomb et al, The complete genome sequence of the gastric pathogen. *Helicobacter pylori* Nature 388:539–547 (1997).

Altman and Kirseborn, "Ribonuclease P," *The RNA World* 2:1155–1184 (1999).

Altman et al., "Recent studies of ribonuclease P," *FASEB Journal* 7:7–14 (1993).

Brown, "The Ribonuclease P Database," *Nucleic Acids Research* 27(1):314 (1999).

Frank and Pace, "RIBONUCLEASE P: Unity and Diversity in a tRNA Processing Ribozyme," *Annu. Rev. Biochem.* 67:153–180 (1998).

Gopalan et al., "Analysis of the functional role of conserved residues in the protein subunit of ribonuclease P from *Escherichia coli*," *J. Mol. Biol.* 267:818–829 (1997).

Hansen et al., "Physical Mapping And Nucleotide Sequence Of the RNPA Gene That Encodes the Protein Component Of Ribonuclease P in *Escherichia Coli*," *Gene*, 38:85–93 (1985).

Kirsebom and Altman, "Reaction in vitro of some mutants of Rnase P with wild–type and temperature–sensitive substrates," *J. Mol. Biol.* 207:837–840 (1989).

Kirsebom and Svard, "The kinetics of specificity of cleavage by Rnase P is mainly dependent on the structure of the amino acid acceptor stem," *Nucleic Acids Res.* 20:425–432 (1992).

Niranjanakumari et al., "Protein component of the ribozyme ribonuclease P alters substrate recognition by directly contacting precursor tRNA," *Proc. Natl. Acad. Sci. USA* 95:15212–15217 (1998).

Pace and Brown, "Evolutionary perspective on the structure and function of ribonuclease P, a ribozyme," *J. Bacteriol.* 177:1919–1928 (1995).

Pascual and Vioque, "Substrate binding and catalysis by ribonuclease P from cyanobacteria and *Escherichia coli* are affected differently by the 3' terminal CCA in tRNA precursors," *Proc. Natl. Acad. Sci. USA* 96:6672–6677 (1999).

Peck–Miller and Altman, "Kinetics of the processing of the precursor to 4.5 S RNA, a naturally occurring substrate for Rnase P from *Escherichia coli*," *J. Mol. Biol.* 221:1–5 (1991).

Sakano et al., "Temperature sensitive mutants of *Escherichia coli* for tRNA synthesis," *Nucleic Acids Research* 1:355–371 (1974).

Stams et al., "Ribonuclease P protein structure: evolutionary origins in the translational apparatus," *Science* 280:752–755 (1998).

Thompson et al., "CLUSTAL W: improving the sensitivity of progressive multiple sequence alignment through sequence weighting, position–specific gap penalties and weight matrix choice," *Nucleic Acids Research* 22:4673–4680 (1994).

* cited by examiner

FIG. 1, Panel A

| SEQ ID NO. | | Residue Number | 10 | 11 | 12 | 13 | 14 | 15 | 16 | 17 | 18 | 19 | ... | 46 | ... | 47 | 48 | 49 | 50 | 51 | 52 | 53 | 54 | 55 | 56 | 57 | 58 | 59 | 60 | 61 |
|---|---|---|---|---|---|---|---|---|---|---|---|---|---|---|---|---|---|---|---|---|---|---|---|---|---|---|---|---|---|---|
| | | Gram Negative Bacteria | | | | | | | | | | | | | | | | | | | | | | | | | | | | | |
| | | gamma purple | | | | | | | | | | | | | | | | | | | | | | | | | | | | | |
| 39 | | *Escherichia coli* (119) | L | L | R | L | T | P | S | Q | F | T | | R | | H | G | L | T | V | A | K | K | N | V | K | R | A | H | E |
| 40 | | *Proteus mirabilis* (119) | L | L | R | L | T | P | K | H | F | N | | R | | L | G | L | T | I | A | K | K | N | L | K | K | R | H | E |
| 41 | | *Haemophilus influenzae* (136) | L | L | K | L | T | P | H | Q | F | K | | R | | L | G | L | T | V | G | K | R | S | H | L | K | R | Y | Q |
| 42 | | *Pseudomonas putida* (133) | K | S | K | L | K | P | R | T | F | Q | | R | | L | G | L | S | H | A | R | K | S | V | R | K | A | Y | R |
| 43 | | *Buchnera aphidicola* (114) | S | L | R | L | T | P | A | A | F | T | | R | | L | G | L | T | V | A | K | K | N | V | K | R | A | H | E |
| 44 | | *Salmonella typhi* (119) | L | L | R | L | T | P | S | S | F | T | | R | | L | G | L | T | V | A | K | K | N | V | K | R | A | H | E |
| 45 | | *Yersinia pestis* (119) | L | L | R | L | T | P | S | H | F | H | | R | | L | G | L | T | V | A | K | K | N | V | K | R | A | H | E |
| 46 | | *Klebsiella pneumoniae* | L | L | R | L | T | P | S | H | F | T | | R | | L | G | L | T | V | A | K | K | N | V | K | R | A | H | E |
| 47 | | *Salmonella paratyphi* | L | L | R | L | A | P | R | S | Y | - | | R | | L | G | L | A | H | P | K | K | Q | I | H | T | A | V | G |
| 48 | | *Vibrio cholerae* | H | L | R | L | T | P | E | H | F | Q | | R | | L | G | L | T | V | A | K | K | N | V | K | R | A | V | Q |
| 49 | | *Pseudomonas aeruginosa* | L | L | R | L | T | P | A | Q | F | S | | R | | L | G | L | A | V | G | K | K | Y | V | H | L | A | N | Q |
| 50 | | *Shewanella putrefaciens* | L | L | R | L | T | P | A | Q | F | K | | R | | L | G | L | T | V | A | K | R | | | | | | | |
| | | alpha purple | | | | | | | | | | | | | | | | | | | | | | | | | | | | | |
| 51 | | *Coxiella burnetii* (121) | W | L | R | H | T | Q | A | E | F | R | | R | | L | G | V | Y | V | S | K | R | N | V | R | K | A | W | V |
| 52 | | *Rickettsia prowazekii* (121) | T | S | L | K | N | R | K | E | F | E | | - | | L | G | H | K | A | S | R | I | L | Z | K | G | A | V | V |
| 53 | | *Caulobacter crescentus* | E | L | R | R | K | R | P | D | F | L | | R | | V | G | F | T | A | T | K | K | F | A | H | G | A | V | E |
| | | epsilon purple | | | | | | | | | | | | | | | | | | | | | | | | | | | | | |
| 54 | | *Helicobacter pylori 26695* (161) | D | S | L | K | N | K | E | E | F | D | | K | | L | G | L | S | V | S | K | K | - | V | G | K | A | V | K |
| 55 | | *Helicobacter pylori J99* (161) | D | S | L | K | K | K | E | E | F | D | | K | | L | G | L | S | V | S | K | K | - | V | G | K | A | V | V | K |
| 56 | | *Campylobacter jejuni* | D | K | P | W | H | N | D | E | P | S | | K | | H | A | V | V | A | G | R | K | - | A | G | K | A | V | V | V |
| | | beta purple | | | | | | | | | | | | | | | | | | | | | | | | | | | | | |
| 57 | | *Neisseria gonorrhoeae* | Y | R | R | L | K | R | R | E | F | A | | R | | H | G | L | V | V | S | K | K | T | K | K | G | R | N | E |
| 58 | | *Neisseria meningitidis* | Y | R | R | L | K | R | R | E | F | A | | R | | H | G | L | V | V | S | K | K | F | K | K | G | R | N | E |
| 59 | | *Bordetella pertussis* | A | R | L | H | R | P | S | D | F | R | | R | | H | G | L | H | V | A | K | K | - | A | K | G | S | Y | R |
| 60 | | *Thiobacillus ferrooxidans* | D | R | L | Q | R | R | S | E | A | I | | R | | H | A | L | V | V | A | K | K | - | V | G | G | N | V | Q |
| | | Gram Positive Bacteria | | | | | | | | | | | | | | | | | | | | | | | | | | | | | |
| | | high G & C | | | | | | | | | | | | | | | | | | | | | | | | | | | | | |
| 61 | | *Streptomyces bikiniensis* (123) | N | R | R | R | R | P | E | D | A | A | | R | | A | G | F | V | V | S | K | A | - | G | V | G | V | A | V |
| 62 | | *Streptomyces coelicolor* (123) | N | R | R | R | T | S | W | E | A | A | | R | | A | G | F | V | V | A | K | A | - | V | A | R | A | V | V |
| 63 | | *Micrococcus luteus* (123) | R | R | R | R | P | S | A | D | E | R | | R | | V | G | F | V | V | A | A | S | - | A | N | G | Z | A | V |
| 64 | | *Mycobacterium tuberculosis* (125) | N | R | M | R | S | A | D | E | D | R | | R | | V | G | F | H | V | A | K | K | - | V | A | G | S | V | V |
| 65 | | *Mycobacterium leprae* (120) | N | R | M | R | S | A | T | E | L | R | | R | | V | G | L | H | V | A | T | K | - | A | A | T | G | V | V | E |
| 66 | | *Mycobacterium bovis* (115) | N | R | M | R | S | S | A | E | D | R | | R | | V | G | F | V | V | G | K | K | - | A | A | G | S | V | V |
| 67 | | *Mycobacterium avium* | N | R | M | R | T | W | S | A | E | D | | R | | V | G | F | V | V | G | R | K | - | W | S | T | F | V | V |
| 68 | | *Corynebacterium diphtheriae* | H | K | E | S | S | W | S | Q | - | R | | R | | F | A | L | V | S | - | R | K | R | A | G | N | A | V | T |

FIG. 1, Panel B

FIG. 1, Panel C

FIG. 1, Panel D

FIG. 2A

*Streptococcus mutans* UAB159 (119 aa)

Amino acid sequence: SEQ ID NO. 20

VLKKAYRVRKSDKDFQAIFTEGRSVANRKFVVYSLEKDQSHYRVGLSVGKRLGNAVVRNAIKRKLRHVLMELGPYLGT
QDFVVIARKGVEELDYSTMKKNLVHVLKLAKLYQEGSIREKE

Nucleotide sequence (plus strand):    SEQ ID NO. 1

AGATTTTGCTTTTCTCATTTTATGATATATAGTGATAATTAAATATTGAGTCATGTTTGAAAAAGCCTA
TCGCGTTAAAAGTGATAAAGATTTCAGGAGCAATTTTACTGAAGACGAAGTGTTGCCAATCGGAAATTTGTTGTCT
ATAGTTAGAAAAAGATCAAAGTCACTATCGTGTTGGACTTTCAGTTGGAAAAAGATTAGGAAATGCTGTCGTTAGA
AATGCGATTAAACGAAAATTGCGCCATGTCCTTATGGAACTTGGTCCTTATTTAGGCACTCAAGATTTTGTTGTTAT
TGCTAGAAAAGGTGTTGAGGAACTTGATTATAGCACGATGAAAAAAAATCTGGTTCATGTTTTAAAACTGGCTAAAC
TGTATCAGGAAGGATCTATTCGTGAAAAGAA

Sequence origin: University of Oklahoma ACGT; Contig 299

FIG. 2B

*Klebsiella pneumoniae* M6H 78578 (119 aa)

Amino acid sequence:   SEQ ID NO. 21

VVKLAFPRELRLLTPSHFTFVFQQPQRAGTPQITILGRLNSLGHPRIGLTVAKKNVKRAHERNRIKRLTRESFRLRQ
HELPPMDFVVVAKRGVADLDNRALSEALEKLWRRHCRLARGS

Nucleotide sequence (plus strand):    SEQ ID NO. 2

CGTCGTCGTGCTCGTCTGCTCCGGCCGCCTCGTCGTCTGACCGTTCCAAGTAATAAAGCTAACCCTGCGTGGTTAAGCTCGCATT
TCCCAGGAGTTACGCTTGTTAACTCCCAGTCATTCGTCTTCCAGCAGCCACAACGGGCTGGCACGCCGC
AAATCACCATCCTCGGCCGCCTGAATTCGCTGGGGCATCCCCGCATCGGTCTCACCGTCGCCAAGAAAAACGTGAAA
CGCGCACATGAACGTCAACGCGATTAAACGTCGACGCGTGACCTCGATAACCGTGCTCTCGGAAGCGTTGGAAAATTAT
GGATTTCGTGGTGCGAAAAGAGGGTTGCCGACCTCGATCGGCCTGATTCGAGTTTATCAGCGCCTGATTAGTCCGCTAC
GGCGCCGCCATTGTCGCCTGGCTCGCGGCCTGGGCCTGGGGTCCTGATCGGCCTGATTCGAGTTTATCAGCGCCTGATTAGTCCGCTAC
TCGGGGCCGCATTGTC

Sequence origin: Washington University; Contig 632

FIG. 2C

*Salmonella paratyphi A* ATCC 9150 (110 aa)
Amino acid sequence:                       SEQ ID NO. 22
VTFVNSRSFHIRLPATSTGCTPQITILGRLNSLGHPRIGLTVAKKNVRRAHERNRIKRLTRESFRLRQHELPAMDFV
VVAKKGVADLDNRALSEALEKLWRRHCRLARGS Nucleotide sequence (plus strand):         SEQ ID NO. 3
CTGACCGTTCCAAGTAATAAAGCTAACCCCTGAGTGGTTAAGCTCGCATTTCCAGGAG*GTTA*CGTTGTTAACTC
CCGCTCATTTCACATTCGTCTTCCAGCAACCTCAAGGGCTGCACGCCGCAAATCACCATCCTCGGCCGCCTGAATT
CGCTGGGGCATCCCCGTCGTCTTACCGTCGCCAAGAAAAATGTTCGACGTGCGCATGAACGCAACCGGATTAAA
CGTCTGACGCGGTGAAAGCTTCCGTCTGCGCCAGCATGAACTTCCTGCAATGGATTCGTGGTGGTGGCGAAAAAAGG
GGTTGCCGACCTCGATAACCGTGCTCTCTCGGAAGCGTTGGAAAAATTATGGCGCCGCCACTGTCGCCTGGCTCGCG
GGTCCTGATAGCCCTTATTCGGTCTATCAACGCCCTGATCAGTCAGTCCGCTGCTTGGGCCGCATTGTCGTTC Sequence origin: Washington University;

FIG. 2D

*Pseudomonas aeruginosa* PAO1 (135 aa)
Amino acid sequence:                       SEQ ID NO. 23
VVSRDFDRDKRLLTARQFSAVFDSPTGKVPGKHVLLLARENGLDHPRLGLVIGKKNVKLAVQRNRLKRLIRESFRHN
QETLAGWDIVVIARKGLGELENPELHQQFGKLWKRLLRNRPRTESPADAPGVADGTHA Nucleotide sequence (plus strand):         SEQ ID NO. 4
TCTGTCGCGTCGTCGCGCCAAAGGCCGTAAGGCGTCTGACCGTTCGATTTATCCGTACGG*GTGT*GAGTCGGGACTT
CGACCGGACAAGCGTCTACTGACAGCCCGGCAATTCAGCGCAGTCTTCGACTCTCCGACCGGCAAGGTCCCCGGCA
AGCACGTCCTGCTGCTGGCGCGCGAGAACGGTCTCGATCACCCCCGCCTGGTGATCGGCAAGAAGAACGTC
AAGCTCGCCGTCCAGCGCAATCGCCGCGCAAATCGCCCTGATCGTTCCGCCATAACCAGAAACCCTGGCTGG
CTGGGATATCGTGGTGATCGCGCGCAAGGCCCTGGGCGCAAATGCGAAAATCCGGAGCTGCACCAGCAGTTCGGCAAGC
TCTGGAAACGTCTGTTGCGCAATCGCCGCGAAAAGCCTCGCACGAAGACCCTGCTGACGCCTGTGCGTTGGCCGACGGTACTCAT
GCATAGGTCGATGCCCGCGCATCCGATCCCTGTAGTGTCATCCCCCTTCGATGACCCGCACCG Sequence origin: Pathogenesis & University of Washington; Contig 54

FIG. 2E

*Corynebacterium diphtheriae* (129 aa)

Amino acid sequence: SEQ ID NO. 24

VTLTSSNRTTVLPSQHKLSNSEQFRATIRKGKRAGRSTVVLHFYAEATAGNLATAGGPRFGLVVSKAVGNAVTRHRV
SRQLRHVVIAMKDQFPASSHVVVRAIPPAATASYEELRADVQAALDKLNRKR

Nucleotide sequence (plus strand): SEQ ID NO. 5

CCGGTCGCGCAATCGTGGCTGCCACGTCGTAACAAGGTCGTAAGAGCCTGACCGCTTAAGGTCACTCTTACAAGCTC
GAATAGAACGACGGTGCTACCTTCACAGCACAAGCTCAGCAATTCCGAGGCAATCCGCGCAACGATTCGGAAGGCA
AGCGTGCTGGGAGGAGCACCGTCGTTCTTCATTTTATGCTGAGGCGACCGCGGGCAACCTTGCAACCGCAGGCGGC
CCGCGATTCGGCCTCGTTGTGTTCCAAGGCTGTGACTGCTGTGAATGCTGTCACCGTCGTCGGCAGTGTTCGGCGCAGTTAAGGCA
CGTAGTAATCGCTATGAAAGACCAGTTCCCAGCGTCATCCCATGTGTTGTGAGGCGATACCGCCAGCGGCGACAG
CAAGTTATGAGGAGTTGCGGGCAGAGTGCAGGCAGCACTCGACAAGCTCAACCGCAAGCGATAAGGCCGGTTACTCG
CCCTCGTGGGCTGGTTAGTCGCGCATTGTTTGATGCGGTGCGGTTCTA

Sequence origin: Sanger centre; Contig 390

FIG. 2F

*Chlamydia trachomatis* MoPn (119 aa)

Amino acid sequence: SEQ ID NO. 25

VHRLTLPKSARLLKRKQFVYVQRCGQYCRTDQATLRIVPSRHSNIRKVGVTVSKKFGKAHQRNRFKRIVREAFRHVR
PNLPACQVVVSPKGGTLPNFGKLSADLLKHIPEALPLVTSSK

Nucleotide sequence (plus strand): SEQ ID NO. 6

GCTACAAAAGTGGAAGAAGAAATCTTTAAATCGTCGTCGCCGTCACGGCAGACATTCCTTAATTGATCTCTAAGATCT
TTCATTGTGCATCGGTTAACTCTACCTAAAGTGCCCGCCTATTGAAACGTAAACAATTGTTTACGTGCAGCGTT
GTGGGCAATATTGTCGTACTGATCAGGCAACTTTACGAATAGTTCCTTCCGTCATTCGAACATCCGTAAAGTAGGG
GTTACTGTTTCTAAAAAATTTGGGAAAGCCCATCAGCGCAATCGCTTTAAAAGAATTGTGCGAGAGCTTTTAGGCA
TGTGCGACCAAATCTTCCCGCATGTCAAGTGGTAGTGTCTCCTAAAGGGGCACTCTACCAAATTTGGTAAACTAT
CCGGGATCTCTTAAGCATATTCCAGAGAGGCATGAATGGGAA
AATAAAAAACCATTCCACGCTATAGAGGCATGAATGGAA

Sequence origin: TIGR & Manitoba University;

FIG. 2G

Vibrio cholerae serotype O1, Biotype El Tor, Strain N16961 (122 aa)
Amino acid sequence:       SEQ ID NO. 26
SRIILSTYAFNRELRLLTPEHYQKVFQQAHSAGSPHLTIIARANNLSHPRLGLAVPKKQIKTAVGRNRFKRICRESF
RLHQNQLANKDFVVIAKKSAQDLSNEELFNLLGKLWQRLSRPSRG
Nucleotide sequence (minus strand):  *NO INITIATOR CODON BEFORE STOP*    SEQ ID NO. 7
GGCAGCGTGGGCCGATAAGTGGACTAATAAACCACTGGTAAAGTTTTACAATAACCAATGGCTAACCACGAGAAGGGC
GAGAGAGGCCGTTGCCATAGTTTGCCAAGCAAGTTAAACAGTTCTTCATTGCTCAAATCTTGCGCGCTCTTTTGGCG
ATGACAACAAAATCTTTGTTAGCCAGTTGATTTTGATGTAAGCGAAAGCTTTCTCTGCAAATACGTTTGAATCGATT
ACGGCCGACGGCAGTTTGATCTGTCTTTTTAGGAACCGCGAGTCCCAAACGAGGATGAGAAAGGTTATTAGCGCGAG
CGATGATTGTGAGATGAGGAGAACCAGCACTGTGAGCTTGCTGCTGAAGACTTTTGATAATGTTCGGAGTTAACAAA
CGTAACTCCCGATTGAATGCGTACGTACTCAAAATAATTCGAGATTATTTTGACAGGCGCTTACGGCCTTTTGCACG
ACGTGCATTCAGAACTTACGACCGTTCGC
Sequence origin: TIGR

FIG. 2H

Neisseria gonorrhoea FA 1090 (123 aa)
Amino acid sequence:       SEQ ID NO. 27
VILDYRFGRQYRLLKTDDFSSVFAPRNRRSRDLLQVSRSNGNGLDHPRIGLVVGKKTAKRANERNYMKRVIRDWFRL
NKNRLPPQDFVVRVRKFDRATAKQARAELAQLMFGNPATGCGKQV       SEQ ID NO. 8
Nucleotide sequence (minus strand):       SEQ ID NO. 8
ATGTTCCTTGTATGGGAAACCCGTTGCCGTCGAACCTTGCCTGCAGGTACCGTTCTGATCATACCTGTTCTCCCGC
ATCCGGTTGCGGGGTTGCCGAACATGAGTTGTGCCAGTTGTGCCAGTTGTGCCTGCCCCTTGCCTGTCTGTCGAATTTC
CGGCGGACGCGCACGACGAAATCCTGAGGCGGCAGCCGGTTTTTGTTCAATCGAACCAGTCGCGGATGACGCGTTT
CATATAGTTCCGCTCGTTGGCGTTTTGCCGACCAGACCGATGCGGGGATGCGGGGATGGTCCAGCCCGT
TGCCGTTGAGCGCGAAACTTGCAGCAGGTCGCGGGTGCGGGTTTCTGAATGCAAAACGGATGAAAAATCATCC
GTTTTTAACAAGCGGTACTGCCTTCCGAAGCGGTAGTCCAAAATTACACTGCCAGGCGTTGCGGCCTTTGGCACGG
CGTGCGGCCAATACTGCCGCTCCGCGCGT
Sequence origin: University of Oklahoma ACGT; Contig 60

FIG. 2I

*Neisseria meningitidis* serogroup A strain Z2491 (123 aa)
Amino acid sequence:  SEQ ID NO. 28
VILDYRFGRQYRLLKTDDFSSVFAFRNRRSRDLLQVSRSNGNGLDHPRIGLVVGKKTAKRANERNYMKRVIRDWFRL
NKNRLPPQDFVVRVRRKFDRATAKQARAELAQLMFGNPATGCRKQA Nucleotide sequence (minus strand):  SEQ ID NO. 9
TGTTCCTTAGTATGGGAAACCCGTTGCCGTCTGAACCTTGCCTGCCAGAGTACCGTTCTGATCATGCCTGTTCCTGC
ATCCGGTTGCGGGGTTGCCGAACATGAGTTGTGCCAGTTCCGCCCTTGCCTGTTTGCGGTAGCCCTGTCGAATTTA
CGGCGGACGCGCACGACGAAATCCTGCGGCGCAGCCGGTTTTGTTCAATCTGAACCAGTCGCGATGACGCGCTT
CATATAATTCGTTCGTTGGCGTTTGGCGTTCGCAGCGTCCGCGGCTGCGCGGGATGATCCAGCCCGT
TGCCGTTGAACGCGAAACTGCAGCAGTCCGCGGCTGCGCGGGTTCTGAATGCAAAACGATGAAAAATCATCC
GTTTCAACAAGCGTACTGCCTTCCGAAGCGGTAGTCCAAAATTACACCGCCAGGCGTTTGCGGCCTTTGGCGCGC
CGTGCGGCCAATACTGCGCGTCCGCCGCGC Sequence origin: Sanger centre & Oxford University

FIG. 2J

*Streptococcus pyogenes* M1 (113 aa)
Amino acid sequence:  SEQ ID NO. 29
VKREKDFQAIFKDGKSTANRKFVIYHLNRGQDHFRVGISVGKKIGNAVTRNAVKRKIRHVIMALGHQLKSEDFVVIA
RKGVESLEYQELQQNLHHVLKLAQLLEKGFESEEKH Nucleotide sequence (minus strand):  SEQ ID NO. 10
GTTACCTCACCACGACCACAGGCCACTAATAATAGAACTAAGGGACTATTCTTGCAATTTAATGTTTTTCTTCAC
TCTCAAAACCTTTCTCAAGCAATTGTGCTAACTTTAAAACATGATGTAAATTTGTTGAAGCTCTTGATACTCCAAA
GATTCGACACCCTTACGGCCAATCACCACCAGCCGAAATCCTCTGACTTCAGCTGCCCTAATGCCATGATAACGACG
TATCTTTCGTTGACTGCATTTCTGGTGACTGCATTTTTACCGACAGAAATACCCACACGGAAGTGT
CTTGGCCTCTATTTAAATGATAAATGACAAATTTCGATTGCTGTGTACTTTTTCCATCCTTAAATATGGCTTGAAA
TCTTTCTCACGCTTGACACGATAGGTCTTCTTCAAAATTAACTCCAATATCTAAATTATTACCATTATACCACCATC Sequence origin: University of Oklahoma ACGT; Contig 7

FIG. 2K

***Bordetella pertussis* Tohama I** (123 aa)

Amino acid sequence: SEQ ID NO. 30
MPRATLPAEARLHRPSEFAAALKGRRLARGAFFIVSASPCAPADDQPARARLGLVIAKRFAARAVTRNTLKRVIREA
FRARRLALPAQDYVVRLHSKLTPASLTALKRSARAEVDAHFTRIAR

Nucleotide sequence (minus strand): SEQ ID NO. 11

CCACCCAGGGGCTGAGGAAGTACCGGTAAAACCGGATCGGGGCGATAAGCAGTCTCCTGATCATCGCGCTATCCGTG
TGAAGTGAGCATCTACTTCGGCGCGCGCCGAGCGTTTCAGGGCCGTGAGGCTTGCCGGTGTCAGCTTGCTGTGCAGC
CGCACCACGTAATCCTGGGCCGGCAGGGCAAGCCGGCGAGCCCGGAACGCTTCGCGGATGACCCGCTTCAAGGTATT
GCGCGTCACGGCGCGGGCGGCAAAACGCTTGGCGATCACCAGGCCCAGGCGCGCGCGCGCCGGCTGGTCATCAGCAG
GGGCACAGGGCGAGGCGCTGACAATAAAGAAAGCCCCTCGGGCCAGTCGCCGGCCTTTGAGGGCGGCGGCAAACTCG
GAGGGGCGATGCAATCGCGCCTCCGCAGGGAGCGTGGCGCGCGGCATGGGTGACGTGACGGAGACTGGCGACGGGGC
CGGCGGCGATGCTCCTGTTACAGGCAATCC

Sequence origin: Sanger centre & MDS; Contig 267

FIG. 2L

***Porphyromonas gingivalis* W83** (137 aa)

Amino acid sequence: SEQ ID NO. 31

MTSPPTFGLSKSERLYLRDEINTVFGEGKAFVVYPLRVVYRLGSEHRVAYSSMLVSVAKKRFRRAVKRNRVKRLVRE
AYRLNKHLLNDVLQERQIYATIAFMVVSDELPDFRTVERAMQKSLIRIAGNVPSSALKNE

Nucleotide sequence (minus strand): SEQ ID NO. 12

AGAAGAAAATGGGGAGCAGTAAGAGTTGCACGAGAAAAGCCTTGATCAGTCGCATCGTATTTACTCGTTTTTCAAAG
CCGATGAAGGTACATTTCCGGCAATTCTGATCAGACTCTTTTGCATCGCTCTCTCCACTGTACGAAAGTCAGGAAGT
TCATCCGATACTACCATAAATGCAATAGTAGCATAGATCTGTCTCTCTTGGAGGACATCGTTCAGGAGGTGTTTGTT
GAGCCGATAAGCCTCCCTGACCAAACGCTTGACCCTATTGCGCTTCACGGCTCGCCTAAACCTTTTCTTTGCTACGC
TTACCAGCATGGAGGAATATGCAACTCGATGCTCCGATCCCAGACGGTAGACTACGCGTAGAGGATAAACGACAAAC
GCCTTGCCTTCGCCAAAGACCGTATTGATTTCATCGCGAAGATAGAGGCGTTCGCTTTTGGATAGGCCGAATGTAGG
CGGAGAGGTCATTTCCCGTTGAGGTAATCCTCTAATGCCATAGCCATAGAAGGATATTGCTCGGTCGGCGCA

Sequence origin: TIGR & Forsyth Dental Center

FIG. 2M

Streptococcus pneumoniae Type 4 (124 aa)

Amino acid sequence: SEQ ID NO. 32

VLKKNFRVKREKDFKAIFKEGTSFANRKFVVYQLENQKNRFRVGLSVSKKLGNAVTRNQIKRRIRHIIQNAKGSLVE
DVDFVVIARKGVETLGYAEMEKNLLHVLKLSKIYREGNGSEKETKVD

Nucleotide sequence (minus strand): SEQ ID NO. 13

TCGCTAGTAGTACCCCATTAGTCGCACAGGCTGTCATGATTAACAGAGACAGTCCTAGCAAACTAGTCAACTTAGTTT
CTTTTCACTCGCCATTCCTTCCCGGTAAATCTTTGATAATTTAATACATGGAGTAGATTTTCTCCATCTCTGCG
TATCCCAAGGTTTCGACTCCTTTTCGAGCAACAAGTCGACATCTTCACCAGACTCCCTTTGCATTCTG
GATAATATGCCGAATCCGTCGCTTAATTTGATTTCTAGTGACGGCATTCCCCAGTTTTTTGCTAACTGATAGACCTA
CTCGAAAACGGTTTTTCTGGTTTTCTAATTGGTAGAGACCACAAATTTGCGATTAGCAAAACTTGTCCCCTCCTGAAA
ATCGCCTAAAATCTTTCTCTCTTTTTACACGAAAGTTTTCTTCAAACTCAACTCCATCTATTAAATTACTACTA
TTATACCATATTTTCAAAAAGCCAATCATAG

Sequence origin: TIGR;

FIG. 2N

Clostridium difficile 630 (epidemic type X) (114 aa)

Amino acid sequence: SEQ ID NO. 33

MDFNRTKGLKKDSDFRKVYKHGKSFANKYLVIYILKNKSDYSRVGISVSKKVGKAITRNRVRRLIKEAYRLNIDEKI
KPGYDIVFIARVSSKDATFKDIDKSIKNLVKRTDISI

Nucleotide sequence (minus strand): SEQ ID NO. 14

TCCTTTAATATATAAATTATTTATTCAAAGTCATTAAGTCATTAACCTCCATATTTATAGCATACATAAATAAATAGAAATATCCG
TTCTTTTAACTAATAATTTTTTATAGACTTGTCTATGTCTTTCATCAATATTAACTGTAGGCTTCTTTATTAATCTTCTTACTCTATT
ACTATATCATATCCAGGCTTAATTTTTCATCAATATTAACTGTAGGCTTCTTTTATTAATCTTCTTACTCTATT
CCTAGTAATAGCTTTTCCTACTTTTGTTTTTTGAAACAGAAATACCTACTACTTCTGATTATTTTAAGTATAT
ATATTACTAAATATTGTTTGCAAAGATTTGCCGTGTTTATATACTTTTCTAAAATCAGAGTCTTTTTTCAACCCT
TTAGTCCTATTAAAGTCCATAGTTAACCTCCATAAACACAGCTATGAATCGTAATTATTTACACAAAAGGCCACCT
TTG

Sequence origin: Sanger centre; Contig 975

FIG. 2O

*Camphylobacter jejuni* NCTC (108 aa)
Amino acid sequence: SEQ ID NO. 34
VKNFDKFSTNEEFSSVYKVGKKWHCEGVIIFYLNSYEKKIAVVASKKVGKAVVRNRSKRILRALFAKFERYLQDGKY
IFVAKNEITELSFSRLEKNLKWGLKKLECFK
Nucleotide sequence (minus strand): SEQ ID NO. 15
AAGCAGCGGGTTTTAAAGGGCTTAAGAATTTCTGATAAAAACGGAGTATTTTTAGGCATATCATTTGAAACATTCTA
GTTTTTTCAATCCCCATTTTAGATTTTTTTCTAACCTAGAAAAAGAAAGTTCAGTGATTTCATTTTTAGCTACAAAA
ATATATTTGCCATCTTGAAGATATCTTTCAAACTTAGCAAACAAAGCTCTTAAAATTCGTTTTGAACGATTTCTAAC
CACTGCTTTTCCAACTTTTTTACTAGCAACAACTGCTATTTTTTTTTCATAACTATTCAGATAAAAAATGATCACAC
CTTCGCAATGCCATTTTTTGCCTACTTTATATACAGATGAAAATTCCTCGTTTGTGCTAAATTTATCAAAATTTTTC
ACACAGCAAGTCTTTTTCTACCTTTAGCGCGTCTTGCATTGATCACTTTGCGACCATTTTTA
Sequence origin: Sanger centre & MDS

FIG. 2P

*Bacillus anthracis* Ames (119 aa)
Amino acid sequence: SEQ ID NO. 35
MKKKHRIKKNDEFQTVFQKGKSNANRQFVVYQLDKEEQPNFRIGLSVSKKIGNAVVRNRIKRMIRQSITELKDEIDS
GKDFVIIARKPCAEMTYEELKKSLIHVFKRSGMKRIKSSVRK
Nucleotide sequence (minus strand): SEQ ID NO. 16
TAAACCTAATTTCTTTTTCAAAGCCTACTCCTCCTTGTATCGGTATGTATATAGTGTAATTCATTTCCTTACGCTAC
TTTTTATTCTTTTCATACCAGAGCGTTTAAAGACATGAATTAAGCTTTTCTTTAATTCTTCATATGTCATCTCTGCA
CAAGGCTTCCTTGCTATTATAACAAAATCTTTTCCAGAATCTATCTCATCTTTTAATTCTGTGATCGACTGGCGAAT
CATACGTTTAATTCGGTTACGCACTACTGCATTTCCTATCTTCTTGCTGACAGAAAGGCCAATACGAAAGTTTGGCT
GCTCTTCTTTATCTAGTTGATAGACAACAAATTGACGATTCGCATTCGATTTTCCTTTTTGAAAAACCGTCTGGAAT
TCATCATTCTTTTTTATACGATGTTTTTTCTT*CAT*ATCAATTGACACTCCTGTAGTTCATCAGCGGAAATTCACTAT
TATTAGAAAAAAAGACCA
Sequence origin: TIGR;

FIG. 2Q

Mycobacterium avium 104 (119 aa)

Amino acid sequence: SEQ ID NO.36

VLPARNRMTRSTEFDATVKHGTRMAQPDIVVHLRRDSEPDDESAGPRVGLVVGKAVGTAVQRHRVARRLRHVARALL
GELEPSDRLVIRALPGSRTASSARLAQELQRCLRRMPAGTGP

Nucleotide sequence (minus strand): SEQ ID NO.17

GTCCGGGGCGACGGTTCGCCCGACCGCCGAATGCCCGCCGCCGACCGCCGGTCCGGTCACGGCCCGGTTCCCG
CCGGCATGCCGCCAGGCACCGCTGCAGTTCCTGCCGCCAGGCGCGCGACGACGGTTCCGGCTTCCGGGCAGCGCG
CGAATCACCAGCCGGTCGAGTTGTTCGAGTTCGCCGAGCAGCAGGCCCCGGGCCAGCAGCCGGCAGCCCACGCG
GTGTCGTTGCACCGCCCGTCCCGACGGCCTTCCGACGACCAGCCGGTGGGCCCCAGCCGTGGGCCGATTCGTCGTCGGGTT
CGGAGTCGCGCCGGAGGTGGACGACGATGTCGGGCTCGCCATGCGGGTTCCGTGCTTCACCGTCGCGTCAAACTCG
GTTGACCGCCGTCATGCCGCCGACCCCCGGTTGCGCCTGCCGTTGCCGCCGGAAGACCCGAAAGACCTGACGTGCGATCAGGCAGGCAGCAGAGAGCCGCGCG
ACCCTTGCGGCCGACC

Sequence origin: TIGR;

FIG. 2R

Staphylococcus aureus NCTC 8325 (117 aa)

Amino acid sequence: SEQ ID NO. 37

MLLEKAYRIKKNADFQRIYKKGHSVANRQFVVYTCNNKEIDHFRLGISVSKKLGNAVLRNKIKRAIRENFKVHKSHI
LAKDIIVIARQPAKDMTTLQIQNSLEHVLKIAKVFNKKIK

Nucleotide sequence (plus strand): SEQ ID NO. 18

GTTATAAGCTCAATAGAAGTTTAAATATAGCTTCAAATAAAACGATAAATAAGCGAGTGATGTTATTGGAAAAAGC
TTACCGAATTAAAAAAGAATGCAGATTTTCAGAGAATAGCAGTAGAATAGTAGATATATAAAAAAGGTCATTCTGTAGCCAACAGACAATTGTTG
TATACACTTGTAATAATAAAGAAATAGACCATTTTCGCTTAGTATTAGTGTTTCTAAAAAACTAGTAATGCAGTG
TTAAGAAACAAGATTAAAAGAGACAATAACGTGAAAATTTCAAAGTACATAAGTCGCATATATTGGCCAAAGATATTAT
TGTAATAGCAAGACAGCCAGCTAAAGATGACGACTTTACAAATAACAGACTTACACGTCTTGAGCACGTACTTAAATTG
CCAAGTTTTAATAAAAAAGATTAAGTAAGGATAGGGTAGGGGGAAGAAAAACATTAACCACTCAACACATCCCGAAG
TCTTACCTCAGA

Sequence origin: University of Oklahoma ACGT; Contig 561

FIG. 2S

*Staphylococcus aureus* COL (117 aa)

Amino acid sequence:      SEQ ID NO. 38

MLLEKAYRIKKNADFQRIYKKGHSVANRQFVVYTCNNKEIDHFRLGISVSKKLGNAVLRNKIKRAIRENFKVHKSHI
LAKDIIVIARQPAKDMTTLQIQNSLEHVLKIAKVFNKKIK

Nucleotide sequence (plus strand):      SEQ ID NO. 19

GTTATAAGCTCAATAGAAGTTTAAATATAGCTTCAAATAAAACGATAAATAAGCGAGTGATGTTATTGGAAAAAGC
TACCCGAATTAAAAGAATGCAGATTTCAGAGAATATAAAAAGGTCATTCTGTAGCCAACAGACAATTGTTG
TATACACTTGTAATAATAAAGAGAAATAGACCATTTCGCTTAGGTATTAGTGTTTCTAAAAAACTAGGTAATGCAGTG
TTAAGAACAAGATTAAAAGAGCAATACGTGAAAATTCAAAGTACATAAGTCGCATATATTGGCCAAAGATATTAT
TGTAATAGCAAGACAGCCAGCTAAAGATATGACGACTTTACAAATACAGAATAGTCTTGAGCACGTACTTAAAATTG
CCAAAGTTTTAATAAAAAGATTAAGTAAGGATAGGGTAGGGGAAGGAAAAACATTAACCACTCAACACATCCCGAAG
TCTTACCTCAGA

Sequence origin: TIGR;

FIG. 3A
*Pasteurella multocida* PM70 (119 aa)
Amino acid sequence:    SEQ ID NO. 50
VIKLNFSRELRLLTPLHFKYVFEQPFRASTPELTILARPNNLAHPRLGLTVAKKHLKKAHDRNRIKRLCRESFRLAQ
YKLPNCDFVIVAKQGIGKLDNRTLTQTLDKLWQRHIRLAQKS Nucleotide sequence (plus strand): SEQ ID NO. 39

*GTG*ATTAAGCTGAATTTTTCGAGGGAGTTACGTTTGTTAACTCCCCTTCATTTTAAATACGTCTTCGAACAGCCGTT
CCGTGCTAGTACACCTGAACTTACCATTCTTGCTCGTCCCAATAATCTCGCTCATCCTCGCTTAGGGTTAACTGTCG
CGAAAAAGCATTTAAAAAAAGCACATGATCGCAATCGCATCAAACGCTTATGCCGAGAAAGTTTCCGCCTAGCACAG
TATAAACTCCCCAATTGCGATTTTGTTATTGTGGCGAAACAGGGAATTGGTAAATTAGACAACAGGACACTCACACA
AACATTGGATAAATTATGGCAAAGACACATTCGCTTAGCTCAAAAATCTTGA

Sequence origin: University of Minnesota Computational Biology Center

FIG. 3B

***Haemophilus ducreyi* strain 35000HP** (123 aa)

Amino acid sequence: SEQ ID NO. 51

VNKLTFSRELRLLAPIQFKAVFEQPYRASTAELTILARQNCVNTPRLGLTVAKKHLKRAHDRNRIKRIVRESFRLKQ
HQLPNFDFVFVAKHGIGKLDNATLFATIDKLWTRHIRLSQQAQSKN

Nucleotide sequence (minus strand): SEQ ID NO. 40

TTAATTTTTGCTTTGTGCTTGTTGACTGAGGCGAATATGACGAGTCCATAATTTATCTATGGTTGCGAAAAGCGTAG
CATTATCTAGTTTACCAATCCCATGCTTGGCAACAAAGACAAAGTCAAAATTAGGTAATTGATGTTGTTTTAAACGG
AAGCTTTCCCGCACAATACGTTTGATCCGATTGCGATCGTGAGCACGTTTTAAATGCTTTTTAGCAACGGTTAACCC
AAGACGAGGCGTATTAACGCAATTTTGACGAGCAAGAATAGTAAGTTCAGCTGTGCTAGCACGATATGGTTGTTCAA
ACACGGCTTTGAATTGAATGGGAGCTAACAAACGTAGCTCCCGAGAAAACGTTAGCTTATT*CAC*

Sequence origin: HTSC (Washington University)

FIG. 3C

*Chlamydia muridarum* (119 aa)

Amino acid sequence: SEQ ID NO. 52

MHRLTLPKSARLLKRKQFVYVQRCGQYCRTDQATLRIVPSRHSNIRKVGVTVSKKFGKAHQRNRFKRIVREAFRHVR
PNLPACQVVVSPKGGTLPNFGKLSADLLKHIPEALPLVTSSK

Nucleotide sequence (plus strand): SEQ ID NO. 41

*GTG*CATCGGTTAACTCTACCTAAAAGTGCCCGCCTATTGAAACGTAAACAATTTGTTTACGTGCAGCGTTGTGGGCA
ATATTGTCGTACTGATCAGGCAACTTTACGAATAGTTCCTTCTCGTCATTCGAACATCCGTAAAGTAGGGGTTACTG
TTTCTAAAAAATTTGGGAAAGCCCATCAGCGCAATCGCTTTAAAAGAATTGTGCGAGAGGCTTTTAGGCATGTGCGA
CCAAATCTTCCCGCATGTCAAGTGGTAGTGTCTCCTAAAGGGGGCACTCTACCAAATTTTGGTAAACTATCCGCGGA
TCTTCTTAAGCATATTCCAGAGGCTTTGCCTCTCGTTACTTCTTCTAAGTAG

Sequence origin: TIGR

FIG. 3D

*Chlamydophila psittaci* (139 aa)

Amino acid sequence: SEQ ID NO. 53

VHRSTLPKYARVLKRKQFLYISRAGSHCQGSQVIFHVAPSRYSGCCKLGITVSKKFGKAHKRNYFKRIVREAFRKKR
HSLPACQIVVMPKNKQQPKFEDLLQDFAQQIPEALSSKLAKNKPTTGVEYSPKNEKCESVLP

Nucleotide sequence (plus strand): SEQ ID NO. 42

*GTG*CATCGATCAACCTTACCCAAATATGCTCGTGTGTtAAAGAGAAAGCAGTTTCTCTACATCTCGCGAGCGGGATC
TCACTGTCAAGGCAGTCAGGTTATTTTTCATGTTGCTCCATCTAGATATTCTGGATGTTGCAAGCTTGGGATAACTG
TCTCAAAAAAATTTGGGAAAGCGCATAAAAGAAATTATTTTAAACGTATTGTGCGCGAGGCTTTTCGTAAAAAGCGT
CACTCTCTTCCTGCTTGTCAAATTGTTGTTATGCCTAAAAACAAGCAGCAACCTAAATTTGAAGATCTGCTTCAAGA
CTTTGCTCAGCAAATTCCAGAAGCACTCAGTAGCAAATTAGCAAAAAATAAGCCTACGACTGGTGTCGAATATAGTC
CAAAGAATGAGAAATGTGAGTCTGTACTTCCTTAG

Sequence origin: TIGR

FIG. 3E

*Treponema denticola* (118 aa)
Amino acid sequence:             SEQ ID NO. 54
VSNFTFSGEERLRDRSCIKAVFQKGLKLSLNGVSLLILPNGLEYNRFLCTFRRGFGSAVMRNRSRRISKEAYRHIKH
RLKTGNDIILLVFSEKDSYSLRLEQLTALFLKAKMYNDEAL
Nucleotide sequence (minus strand):           SEQ ID NO. 43
TCATAAAGCCTCATCATTATACATTTCGCTTTAAAAGAGGGCGGTAAGTTGTTCTAAACGAAGAGAATAAGAAT
CCTTTCTGAAAAAACCAGCAGGATAATGTCGTTTCCCGTTTTAACCTATGTTTATATGTCTATAGGCCTCTTT
GATATTCTCCGAGACCTGTTCCGCATCACTGCGGAACCTCGTCGAAAAGTACATAAGAATCGATTGTACTC
CAATCCATTAGGCAGGATTAACAAACTAACTCCGTTTAAGCTAAGTTTAAGACCCTTTTTGAAATACGGCCTAATAC
ATGACCGATCCCTTAACCGTTCTTCACCGGAAAATGTAAAATTACTCAC
Sequence origin: TIGR

FIG. 3F

*Enterococcus faecalis* (118 aa)
Amino acid sequence:             SEQ ID NO. 55
MKKSYRVKKEKEFQQVFNKKQSCANRRFVVYVLEKPQQAHFRVGISVGKKIGNAVTRNAVKRKIRASLFQLKDRISP
EIDFIVIARPGLEKLSSEEVKANLTHVLNLAKILDVREGIE
Nucleotide sequence (minus strand):           SEQ ID NO. 44
CTACTCAATTCCCTCTCTTACATCTAATATTTAGCTAAATTAACACATGTGTTAAATTAGCTTTCACTTCTTCAG
ACGATAACTTTCCAATCCTGACGTGCAATCACGATAAATCAATTCTGGAGAGATACGGTCTCTTTAATTGAAAT
AAACTCGCGCGGATTTCCGCTTCACAGCATTCTTGTGACCGCGTTTCTTCCCAACAGAAATCCCCAC
TCGAAAATGGCTTGCTTGTGTGTTTCTCTAAAACGTACACCACGAAACGACGATTTGCACAAGATTGTTTTATTAA
ACACCTGTTGAAATTCTTTTCTTTTCTTGACACGGTAGGACTTTTTCAT
Sequence origin: TIGR

FIG. 3G

*Legionella pneumophila* (109 aa)

Amino acid sequence: SEQ ID NO. 56

QPHRLLKKNHFDFVFQSAKKIPTDDFIFLFRENKLGYARLGLALSKKMIAKAHDRNRIKRLLRESFRHTNLPAVDII
ILARPGLAKKTNLGINTKLNKTWEKLASCYGK

Nucleotide sequence (minus strand): *NO INITIATOR CODON BEFORE STOP* SEQ ID NO. 45

CTATTTGCCGTAGCATGAGGCTAATTTTTCCCATGTTTTATTTAATTTAGTATTTATACCTAAATTGGTTTTCTTTG
CTAGACCTGGTCTTGCCAAAATGATTATATCTACAGCAGGCAAGTTAGTATGACGAAAACTTTCTCTAAGTAGCCGT
TTAATGCGATTTCTGTCATGAGCCTTAGCTATCATTTTTTTGACAATGCTAAACCAAGGCGTGCATAGCCTAACTT
ATTTTCTCTGAAAAGGAAAATAAAGTCATCTGTAGGTATTTTTTTCGCGCTTTGAAACACGAAGTCAAAATGATTTT
TTTTTAATAAGCGGTGCGGCTG(STOP)

Sequence origin: Columbia Genome Center

FIG. 3H

*Staphylococcus epidermis* (115 aa)

Amino acid sequence: SEQ ID NO. 57

MEKAYRIKRNSDFQAIYKNGKSVANRQFVVYTYKNRDLKHFRLGISVSKKLGNAVTRNRIKRAIRENFKVHKQNIIA
KDIIVIARQPAKDMNTLEIQSSLEHVLKIAKVFNKKIK

Nucleotide sequence: SEQ ID NO. 46

CTACTTAATCTTTTTATTAAACACTTTTGCAATTTTAAGCACATGCTCTAAACTGCTTTGAATCTCCAGTGTATTCA
TATCTTTTGCTGGTTGCCTCGCAATAACTATAATATCTTTAGCGATAATATTTTGCTTATGCACTTTAAAATTCTCT
CTTATCGCTCTTTTAATTCTATTTCTTGTAACAGCGTTGCCCAGTTTTTTTGAGACACTTATTCCTAAGCGAAAATG
TTTTAAATCTCTATTTTTATAGGTATAGACAACAAATTGTCTATTTGCAACAGACTTCCCATTCTTGTATATCGCTT
GAAAGTCTGAATTTCTCTTAATACGATATGCTTTTTC*CAT*

Sequence origin: TIGR

FIG. 3I

*Mycobacterium smegmatis* (130 aa)

Amino acid sequence: SEQ ID NO. 58

VLPARNRMRRSAEFSVTVSRGVRAAQPDVVVHALRLESNAGNAGDDGDDGDANGPRIGLIVSKAVGNAVERHRVSRR
LRHVAKTFVSGLDPADLIVIRARPSSRDATSSRLERQLGQALERVSSKRRASP

Nucleotide sequence: SEQ ID NO. 47

TCATGGGGACGCCCTGCGCTTCGAGCTCACCCGCTCGAGCGCTTGACCCAACTGTCGTTCCAAACGGGACGACGTGG
CGTCACGACTGCTCGGCCTGGCCCGGATCACGATGAGATCGGCAGGGTCAAGACCGGATACGAACGTTTTGGCGACG
TGCCGCAGACGGCGGGACACGCGGTGACGCTCCACCGCGTTGCCGACGGCTTTGGACACGATCAGACCGATCCGCGG
CCCGTTCGCGTCGCCGTCATCGCCGTCATCGCCGGCATTGCCTGCGTTGCTTTCAAGGCGCAACGCGTGTACGACGA
CATCGGGTTGCGCGGCACGCACGCCGCGACTGACGGTGACACTGAACTCCGCGGACCGCCTCATCCGGTTTCGAGCC
GGAAGCAC

Sequence origin: TIGR

FIG. 3J

*Burkholderia pseudomallei* (97 aa)

Amino acid sequence: SEQ ID NO. 59

VRGSIPLQASAAFPKAARLLKTDEFSSVFRLRPWRRTAHFVIYGKPTGRDARLGLVIGKKYAARAVTRNLVKRLARE
AFRTRRAEFAGWDILLRLHA

Nucleotide sequence: SEQ ID NO. 48

CGCATGCAGGCGCAGCAGAATGTCCCAGCCGGCGAACTCGGCGCGACGCGTACGAAAC
GCCTCGCGGGCGAGCCGCTTGACCAGATTGCGCGTCACCGCACGCGCGGCGTACTTCTTG
CCGATGACGAGCCCAAGACGCGCATCGCGCCCCGTCGGCTTGCCGTAGATCACGAAGTGC
GCGGTGCGCCGCCAGGGACGCAAACGAAAAACGGATGAGAATTCATCCGTTTTCAGAAGT
CGCGCAGCTTTGGGGAAGGCGGCGGACGCTTGCAACGGAATCGAACCCCGGAC

Sequence origin: Sanger Center

FIG. 3K

*Ureaplasma urealyticum* (113 aa)

Amino acid sequence:     SEQ ID NO. 60

MANFISLKKNEDILDTIKKQQKIHSNQIVVYFRKTNLKNVRLAISISKKKFKLATQRNRIRRLIKAWFIAADIPIKS
YDIVVLVKPSFIDGSFVLNCNNLKIILQRIINKEKR

Nucleotide sequence (minus strand):     SEQ ID NO. 49

<u>TTA</u>TCTTTTTCTTTGTTAATAATTCGTTGAAGAATTATTTAAGATTATTACAATTAAAACAAAAGAACCATCAA
TAAACGATGGTTCACTAAGACTACAGCACTACAATATCATAACTTTTAATGGGAATATCAGCAGCAATAACCATGCTTTAATC
AGGCGTCGAATTCGATTGCGTTGTCGTGCTAATTAAACTTTTTTTAGAAATGCTTATAGCTAAGCGAACATTTT
TAGATTGGTTTTACGAAAATAAACTACGATTTGATTAGAATGAATTTTTGTTTCTTAATTGTATCAAGTATAT
CTTCATTTTTTTAGACTAATAAAATTAGC<u>CAT</u>

Sequence origin: University of Alabama at Birmingham

BACTERIAL RNASE P PROTEINS AND THEIR USE IN IDENTIFYING ANTIBACTERIAL COMPOUNDS

CROSS REFERENCE TO RELATED APPLICATIONS

This application is a continuation-in-part of U.S. Ser. No. 09/516,061, filed Mar. 1, 2000.

BACKGROUND OF THE INVENTION

This invention relates to novel bacterial ribonuclease P protein subunits and their use as targets in screening assays to identify compounds useful as antibacterial agents.

Ribonuclease P (RNase P) is an endoribonuclease that cleaves the 5'-terminal leader sequences of precursor tRNAs. RNase P has been characterized in a representative number of species.

In bacteria, the structure of the RNase P holoenzyme is composed of a catalytic RNA subunit (350–450 nucleotides; encoded by the rnp B gene) and a single protein subunit (110–160 amino acids; encoded by the rnp A gene); both are essential for in vivo activity. In Escherichia coli (E. coli) the RNA subunit is termed M1 and the protein subunit is C5. The C5 protein engages in specific interactions with the M1 RNA to stabilize certain M1 RNA conformations. Through these interactions with M1, C5 plays a critical role in the recognition/binding of some substrates.

Comparison of RNase P protein subunits between bacterial species reveals that their primary structures have only a moderate degree of identity. For example, the protein subunits of Bacillus subtilis (B. subtilis) and E. coli are 30% identical. The functional significance of some conserved amino acid residues has been confirmed by mutagenesis studies which have shown that these conserved amino acids play a significant role in the catalytic function of the RNase P holoenzyme.

The tertiary structure of the RNase P protein subunit expressed in B. subtilis has been determined by X-ray crystallography. The overall topology of α-helices and β-sheets is α1 β2 β3 α2 β4 α3, with an uncommon β3 α2 β4 cross-over connection that may confer specific functional consequences. Another functional aspect of the protein is the long loop connecting β2 to β3, termed the metal binding loop, which binds $Zn^{2+}$ ions and mediates interlattice contacts. In addition, the crystal structure reveals an overall fold that is similar to the ribosomal protein S5, translational elongation factor EF-G (domain IV), and DNA gyrase.

Many pathogens exist for which there are few effective treatments, and the number of strains resistant to available drugs is continually increasing. Accordingly, novel compositions and methods for assaying RNase P function would be useful for identifying antimicrobial compounds against these pathogens.

SUMMARY OF THE INVENTION

Certain RNase P amino acid positions are markedly conserved, as revealed by comparing the protein subunit sequences using the ClustalW multiple alignment program, indicating that the residues may be important in RNase P function. The invention features novel polypeptides related to the protein component of the RNase P holoenzyme in several pathogenic bacterial species, as well as the nucleic acid sequences which encode these proteins. The invention also features methods of using these sequences to identify additional RNase P nucleic acids and proteins, and methods to screen for compounds which inhibit RNase P function. Such compounds can be used as antibacterial agents.

In the first aspect, the invention features an isolated polypeptide comprising an RNase P consensus sequence, where the polypeptide has RNase P protein activity. In a preferred embodiment of this aspect, the polypeptide comprises the amino acid sequence of any of SEQ ID NOS: 20–38 or 50–60.

In the second aspect, the invention features an isolated nucleic acid sequence, wherein the sequence encodes a polypeptide comprising an amino acid sequence substantially identical to an amino acid sequence containing an RNase P consensus and has RNase P protein activity. In preferred embodiments, the sequence encodes a polypeptide comprising an amino acid sequence selected from any of SEQ ID NOS: 20–38 or 50–60 and/or the sequence is selected from any of SEQ ID NOS: 1–19 or 39–49.

In the third aspect, the invention features a transgenic host cell including a heterologous nucleic acid sequence encoding the polypeptide of the first aspect of the invention.

In the fourth aspect, the invention features an antibody that specifically binds to the polypeptide of the first aspect of the invention. Preferably the antibody binds to the polypeptide of any of SEQ ID NOS: 20–38 or 50–60.

In the fifth aspect, the invention features a method of identifying an antibiotic agent, the method including: i) contacting an RNase P holoenzyme comprising the polypeptide of the first aspect of the invention with an RNase P substrate in the presence and in the absence of a compound; and ii) measuring the enzymatic activity of the holoenzyme; wherein a compound is identified as an antibiotic agent if the compound produces a detectable decrease in RNase P enzymatic activity as compared to activity in the absence of the compound. In various preferred embodiments, the polypeptide is substantially identical to a polypeptide of SEQ ID NOS: 20–38 or 50–60, the activity is measured by fluorescence spectroscopy, the RNase P substrate is fluorescently tagged $ptRNA^{Gln}$, the fluorescence analysis is carried out in a buffer comprising 10–40 μg/ml carbonic anhydrase and 10–100 μg/ml polyC, or the buffer further includes at least one of the following: 0.5–5% glycerol; 10–100 μg/ml hen egg lysozyme; 10–50 μg/ml tRNA; or 1–10 mM DTT.

In the sixth aspect, the invention features a method for making a $ptRNA^{Gln}$ that includes annealing two RNA fragments together by heating to about 65° C. to about 80° C. for about 5 minutes, followed by cooling to 20–25° C.

In the seventh aspect, the invention features a method of identifying an antibiotic agent, involving contacting an RNase P holoenzyme containing an RNase P consensus sequence, where the holoenzyme has RNase P protein activity, with an RNase P substrate in the presence and in the absence of a compound; and measuring the enzymatic activity of the holoenzyme, where the measuring involves determining the fluorescence polarization level of a fluorescently tagged oligonucleotide that hybridizes to the nucleotide sequence cleaved by the holoenzyme or the intact substrate. A compound is identified as an antibiotic agent if the compound produces a detectable decrease in RNase P enzymatic. activity as compared to the activity in the absence of the compound. In a preferred embodiment, the polypeptide is substantially identical to a polypeptide of any of SEQ ID NOS: 20–38 or 50–60. In another preferred embodiment, the RNase P substrate is $ptRNA^{Gln}$. In still another preferred embodiment, the RNase P holoenzyme contains N. gonorrhea RNase P.

In the eighth aspect, the invention features a method of identifying an RNase P polypeptide consensus sequence, involving identifying a polypeptide that has sequence identity to an RNase P polypeptide; and determining if the polypeptide conserves at least nine of the following twenty amino acids in the *E. coli* RNase P protein sequence: R11, L12, F18, R46, G48, V51, K53, K54, A59, V60, R62, N63, K66, R67, R70, L80, D84, V86, L101, and L105. A polypeptide that does conserve at least nine of the above twenty amino acids in the *E. coli* RNase P protein sequence is a polypeptide with an RNase P consensus sequence.

In the ninth aspect, the invention features another method of identifying a nucleic acid molecule encoding an RNase P polypeptide consensus sequence, involving identifying a nucleic acid molecule that has sequence identity to a nucleic acid molecule encoding an RNase P polypeptide; and determining if the polypeptide encoded by the nucleic acid molecule conserves at least nine of the following twenty amino acids in the *E. coli* RNase P protein sequence: R11, L12, F18, R46, G48, V51, K53, K54, A59, V60, R62, N63, K66, R67, R70, L80, D84, V86, L101, and L105, wherein a nucleic acid molecule encoding a polypeptide that does conserve at least nine of the twenty above amino acids in the *E. coli* RNase P protein sequence is a nucleic acid molecule encoding an RNase P polypeptide consensus sequence.

The term "nucleic acid" encompasses both RNA and DNA, including cDNA, genomic DNA, complementary antisense nucleic acids capable of decreasing RNase P activity, and synthetic (e.g., chemically synthesized) DNA. The nucleic acid may be double-stranded or single-stranded. Where single-stranded, the nucleic acid may be a sense strand or an antisense strand.

By "isolated nucleic acid" is meant a DNA or RNA that is separated from the coding sequences with which it is naturally contiguous (one on the 5' end and one on the 3' end) in the genome of the organism from which it is derived. Thus, in one embodiment, an isolated nucleic acid includes some or all of the 5' and/or 3' non-coding (e.g., promoter) sequences which are immediately contiguous to the coding sequence. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "isolated polypeptide" is meant a preparation which is at least 60% by weight (dry weight) the polypeptide of interest. Preferably the preparation is at least 75%, more preferably at least 90%, and most preferably at least 99%, by weight the polypeptide of interest Purity can be measured by any appropriate standard method, e.g., column chromatography, polyacrylamide gel electrophoresis, or HPLC analysis.

Moreover, an "isolated" nucleic acid or polypeptide is meant to include fragments which are not naturally occurring as fragments and would not be found: in the natural state.

By "a polypeptide containing RNase P activity" is meant a polypeptide sequence that, when combined with an RNA subunit to form an RNase P holoenzyme, has 20%, 50%, 75%, or even 100% or more, of the enzymatic activity of an *E. coli* or *B. subtilis* RNase P holoenzyme. Preferably, the RNA subunit is from the same species when activity is tested. The enzymatic activity can be assessed, for example, by measuring hydrolysis of an RNase P substrate. Standard methods for conducting such hydrolysis assays are described herein and in the literature (see, e.g., Altman and Kirsebom, Ribonuclease P, *The RNA World*, $2^{nd}$ Ed., Cold Spring Harbor Laboratory Press, Cold Spring Harbor, N.Y., 1999; Pascual and Vioque, Proc. Natl. Acad. Sci. 96: 6672, 1999; Geurrier-Takada et al., Cell 35: 849, 1983; Tallsjö and Kirsebom, Nucleic Acids Research 21: 51, 1993; Peck-Miller and Altman, J. Mol. Biol. 221: 1, 1991; Gopalan et al., J. Mol. Biol. 267: 818, 1997; and WO 99/11653).

By "RNase P substrate" is meant a substrate in which hydrolysis by an RNase P holoenzyme requires the presence of the RNase P protein subunit.

By "identity" is meant the relationship between two or more polypeptide sequences or two or more nucleic acid sequences, as determined by comparing the degree of sequence relatedness. "Identity" can be readily calculated by known methods, including but not limited to those described in *Computational Molecular Biology*, Lesk, A. M., ed, Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, Academic Press, 1987; and *Sequence Analysis Primer*, Gribskov, and Devereux, eds., M. Stockton Press, New York, 1991; and Carillo and Lipman, SIAM J. Applied Math. 48: 1073, 1988.

Methods to determine identity are designed to give the largest match between the sequences tested. Moreover, methods to determine identity are available in publicly available computer programs. Computer program methods to determine identity between two sequences include, but are not limited to, the GCG program package (Devereux et al., Nucleic Acids Research 12(1): 387, 1984), BLASTP, BLASTN, and FASTA (Altschul et al., J. Mol. Biol. 215: 403 (1990). The well known Smith Waterman algorithm may also be used to determine identity. The BLAST program is publicly available from NCBI and other sources (*BLAST Manual*, Altschul, et al., NCBI NLM NIH Bethesda, Md. 20894). Searches can be performed in URLs, such as the following:
http://www.ncbi.nlm.nih.gov/BLAST/unfinishedgenome.html; or http://www.tigr.org/cgi-bin/BlastSearch/blast.cgi.

As an illustration of percent identity, if a test nucleic acid sequence (TN) has 95% identity to a reference nucleic acid sequence (RN) at the specified bases, then TN is identical to RN at the specified bases, except that TN may include point mutations in 5% of the total number of nucleic acids present in RN. Thus, 5% of nucleic acids found in RN may be deleted or substituted with another nucleic acid. In addition, the sequence of TN may contain, as compared to the. specified RN bases, insertions of nucleic acids totaling up to 5% of the nucleic acids present in RN. These mutations, as compared to the RN sequence, may occur at the 5' or 3' terminal positions or anywhere between those terminal positions, interspersed either individually among the specified nucleic acids or in one or more contiguous groups of specified nucleic acids. As in the present invention, for nucleic acids encoding proteins, trinucleotide sequences encoding the same amino acid may optionally be treated as identical.

Analogously, a test polypeptide (TP) has an amino acid sequence 95% identical to a reference amino acid sequence (RP) if TP is identical to RP at the specified amino acids, except that TP contains amino acid alterations totaling 5% of the total number of specified amino acids in RP. These alterations include deletions of amino acids or substitutions with one or more other specified amino acids. In addition, the alterations include insertions of other amino acids totaling up to 5% of the total amino acids present in the specified RP amino acids. The alterations in the TP amino acid sequence as compared to the RP sequence may occur at the amino or carboxy terminal positions, or anywhere between those terminal positions, interspersed either individually among residues or in one or more contiguous groups.

By "an RNase P consensus sequence" is meant a sequence which, when aligned to the *E. coli* RNase P sequence using the ClustalW program and performing a comparison of the specified amino acid sequences, shows conservation of at least nine of the following specified 20 amino acid residues in the *E. coli* RNase P protein subunit: R11, L12, F18, R46, G48, V51, K53, K54, A59, V60, R62, N63, K66, R67, R70, L80, D84, V86, L101, and L105. Preferably, the consensus sequence conserves at least 13 of the 20 residues. It is also preferred that the aligned consensus sequence contain at least seven of the following subset of nine amino acid residues in the *E. coli* RNase P protein: F18, R46, K53, A59, R62, N63, K66, R67, R70, more preferably, at least eight of the amino acids, and, most preferably, all nine amino acids of the above subset. For the purpose of determining identity in the present invention, identity of amino acids other than those for which the amino acid is specified in the consensus sequence are ignored in the comparison when calculating identity of nucleic acids encoding an RNase P consensus sequence, and degenerate codons encoding the designated amino acid are treated as identical.

The RNase P sequences claimed as part of the present invention specifically exclude those sequences in the RNase P database (James W. Brown, The Ribonuclease P Database, Nucleic Acids Research 27(1):314 (1999)) as posted on the Internet on Mar. 1, 2000. Also excluded are the RNase P polypeptides and nucleic acids described by nucleic acid or amino acid sequence in EP 0811 688 A2 (*Staphylococcus aureus*) and WO 99/11653 (*S. pneumoniae*).

A "substantially identical" RNase P sequence is one which has or encodes a polypeptide having at least 95% identity, preferably 100% identity, to the twenty amino acids provided from the sequence of *E. coli* RNase P hereinbefore above.

"Transformation" or "transfection" means any method for introducing foreign molecules, such as nucleic acids, into a cell. Lipofection, DEAE-dextran-mediated transfection, microinjection, protoplast fusion, calcium phosphate precipitation, retroviral delivery, electroporation, and biolistic transformation are just a few of the methods known to those skilled in the art which may be used These techniques may be applied for the transformation or transfection of a wide variety of cell types and intact tissues including, without limitation, intracellular organelles (e.g., and mitochondria and chloroplasts), bacteria, yeast, fungi, algae, animal tissue, and cultured cells.

By "transgenic host cell" means a cell (or a descendent of a cell) transformed or transfected with a heterologous nucleic acid sequence comprising a coding sequence operably linked to one or more sequence elements, e.g., a promoter, which directs transcription and/or translation such that the heterologous coding sequence is expressed in said host cell. The transgenic host cells may be either stably or transiently transfected.

By "operably linked" is meant that a selected nucleic acid is positioned adjacent to one or more sequence elements, e.g., a promoter, which directs transcription and/or translation of the selected nucleic acid.

By "specifically binds" is meant an antibody that recognizes and binds to a full length RNase P protein or subfragment, for example, any one of SEQ ID NOS: 20–38 or 50–60, but which does not substantially recognize and bind to other molecules in a sample, including other RNase P proteins.

Other features and advantages of the invention will be apparent from the following detailed description and from the claims.

DESCRIPTION OF THE FIGURES

Figure 1:
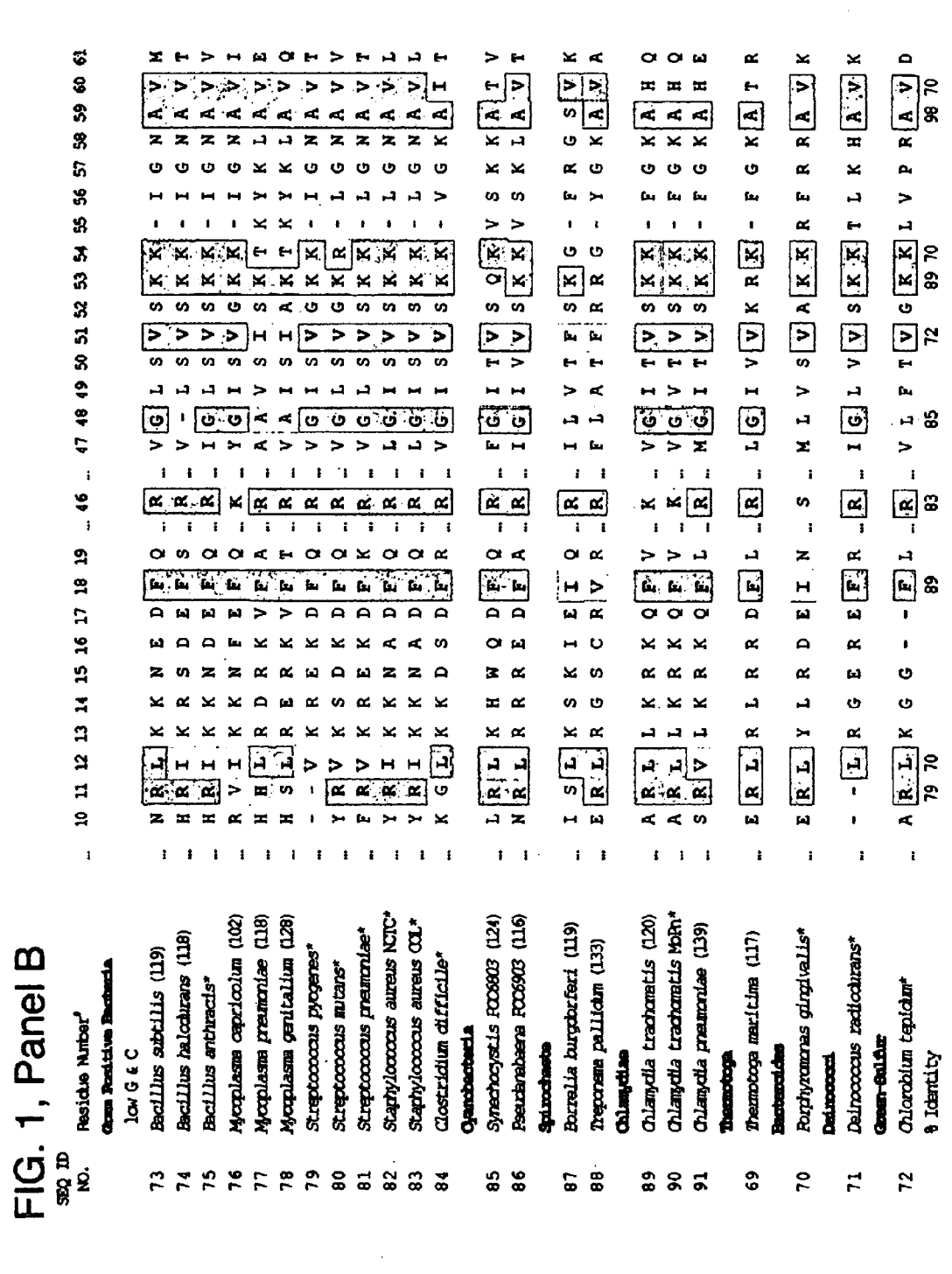
Figure 1:
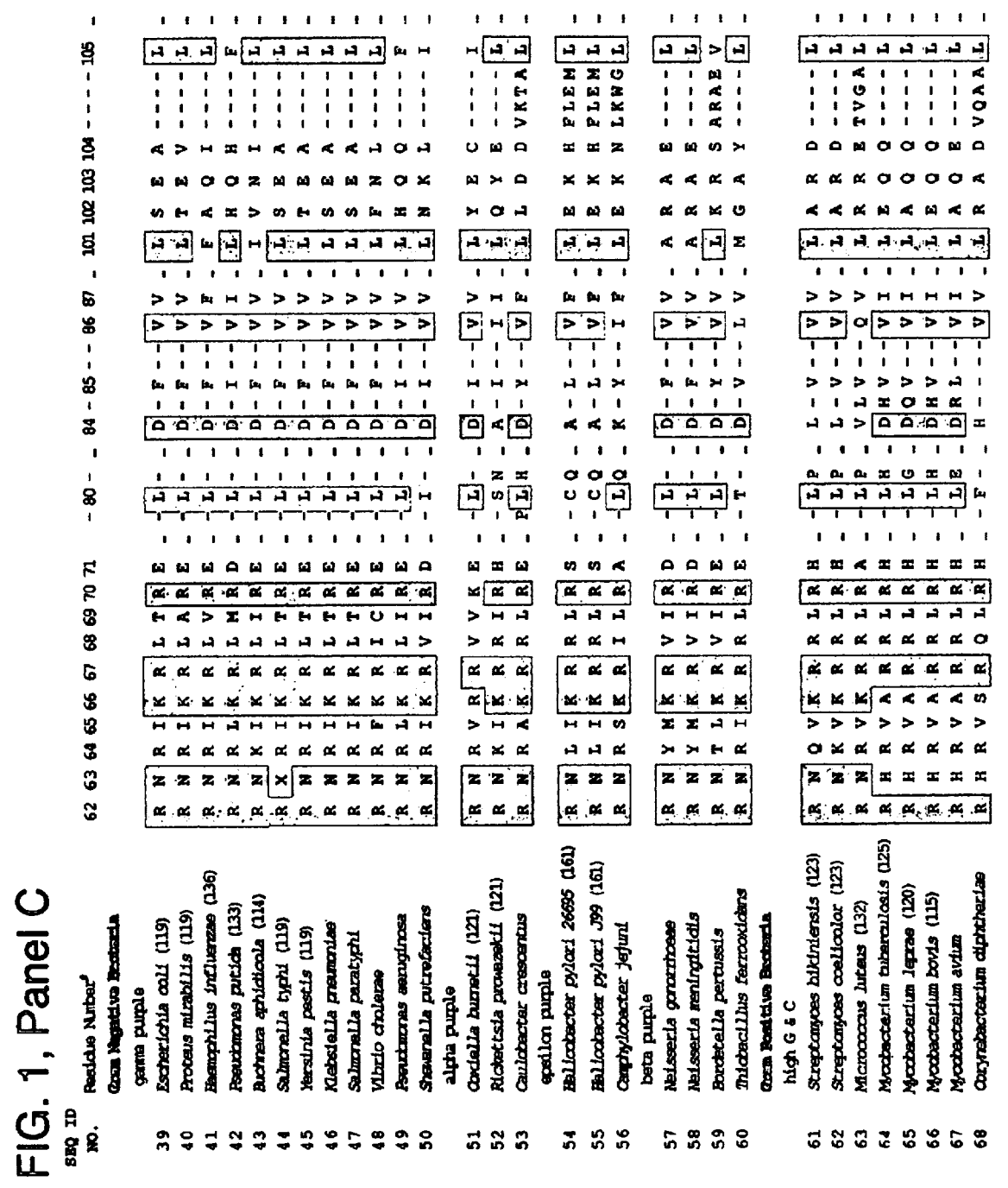
Figure 1:
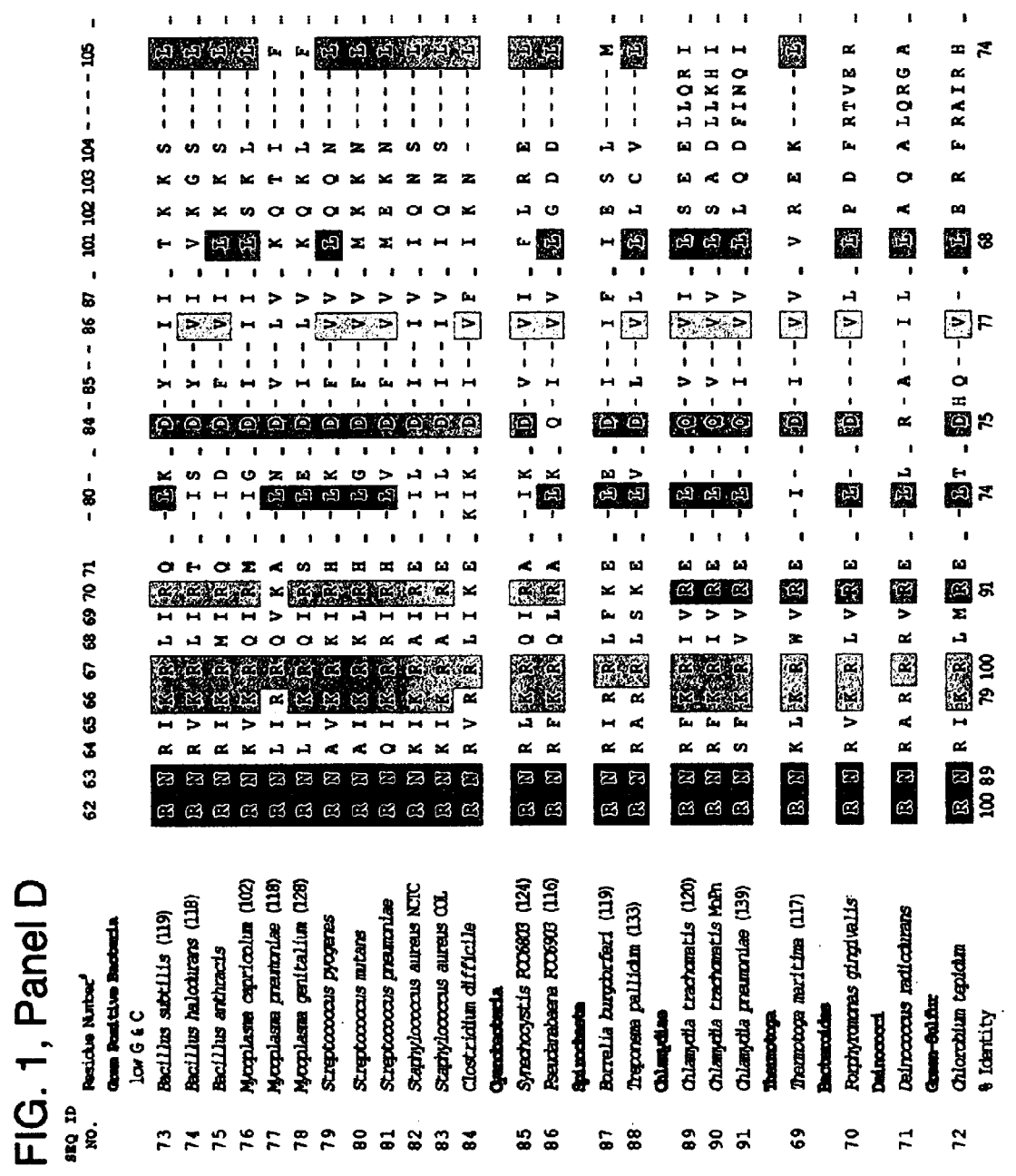

FIG. 1 shows the sequence alignment of previously known bacterial RNase P protein subunits using the ClustalW alignment program (Thompson et al., Nucleic Acids Research 22: 4673, 1994) and the alignment of the RNase P sequences of the present invention.

FIGS. 2A–2S shows the nucleic acid sequences (SEQ ID NOS: 1–19) encoding the amino acid sequences (SEQ ID NOS: 20–38) of the bacterial RNase P polypeptides of the invention. The nucleic acid and amino acid sequences were derived from the following pathogenic bacterial species: *Streptococcus mutans* (FIG. 2A; SEQ ID NOS: 1 and 20, respectively); *Klebsiella pneumoniae* (FIG. 2B; SEQ ID NOS: 2 and 21, respectively); *Salmonella paratyphi* A (FIG. 2C; SEQ ID NOS: 3 and 22, respectively); *Pseudomonas aeruginosa* (FIG. 2D; SEQ ID NOS: 4 and 23, respectively); *Corynebacterium diphtheriae* (FIG. 2E; SEQ ID NOS: 5 and 24, respectively); *Chlamydia trachomatis* (FIG. 2F; SEQ ID NOS: 6 and 25, respectively); *Vibrio cholerae* Serotype 01, Biotype El Tor, Strain N16961 (FIG. 2G; SEQ ID NOS: 7 and 26, respectively); *Neisseria gonorrhoea* FA 1090 (FIG. 2H; SEQ ID NOS: 8 and 27, respectively); *Neisseria meningitidis* Serogroup A, Strain Z2491 (FIG. 2I; SEQ ID NOS: 9 and 28, respectively); *Streptococcus pyogenes* M1 (FIG. 2J; SEQ ID NOS: 10 and 29, respectively); *Bordetella pertussis* Tohama I (FIG. 2K; SEQ ID NOS: 11 and 30, respectively); *Porphyromonas gingivalis* W83 (FIG. 2L; SEQ ID NOS: 12 and 31, respectively); *Streptococcus pneumoniae* Type 4 (FIG. 2M; SEQ ID NOS: 13 and 32, respectively); *Clostridium difficile* 630 (FIG. 2N; SEQ ID NOS: 14 and 33, respectively); *Camphylobacter jejuni* NCTC (FIG. 2O; SEQ ID NOS: 15 and 34, respectively); *Bacillus anthracis* Ames (FIG. 2P; SEQ ID NOS: 16 and 35, respectively); *Mycobacterium avium* 104 (FIG. 2Q; SEQ ID NOS: 17 and 36, respectively); *Staphylococcus aureus* NCTC 8325 (FIG. 2R; SEQ ID NOS: 18 and 37, respectively); and *Staplylococcus aureus* COL (FIG. 2S; SEQ ID NOS: 19 and 38, respectively).

FIGS. 3A–3K shows the nucleic acid sequences (SEQ ID NOS: 39–49) encoding the amino acid sequences (SEQ ID NOS: 50–60) of additional bacterial RNase P polypeptides of the invention. The nucleic acid and amino acid sequences were derived from the following pathogenic bacterial species: *Pasteurella multocida* PM70 (FIG. 3A; SEQ ID NOS: 39 and 50, respectively); *Haemophilus ducreyi* strain 35000HP (FIG. 3B; SEQ ID NOS: 40 and 51, respectively); *Chlamydia muridarum* (FIG. 3C; SEQ ID NOS: 41 and 52, respectively); *Chlamydophila psittaci* (FIG. 3D; SEQ ID NOS: 42 and 53, respectively); *Treponema denticola* (FIG. 3E; SEQ ID NOS: 43 and 54, respectively); *Enterococcus faecalis* (FIG. 3F; SEQ ID NOS: 44 and 55, respectively); *Legionella pneumophila* (FIG. 3G; SEQ ID NOS: 45 and 56, respectively); *Staphylococcus epidermis* (FIG. 3H; SEQ ID NOS: 46 and 57, respectively); *Mycobacterium smegmatis* (FIG. 3I; SEQ ID NOS: 47 and 58, respectively); *Burkholderia pseudomallei* (FIG. 3J; SEQ ID NOS: 48 and 59, respectively); and *Ureaplasma urealyticum* (FIG. 3K; SEQ ID NOS: 49 and 60, respectively).

DETAILED DESCRIPTION

The invention features novel polypeptides that form the protein component of the RNase P holoenzyme in several pathogenic bacterial species, as well as the nucleic acid sequences which encode these proteins. The invention also features methods of using these sequences to form the protein subunit of RNase P holoenzymes to screen for compounds which inhibit the function of the holoenzymes. Such inhibitory compounds can be used as anti-bacterial agents.

1. Identification of the Novel RNase P Protein Subunits

The novel RNase P amino acid and nucleic acid sequences were discovered using the following strategy. First, the genomic databases of several pathogenic bacteria were searched using the BLAST program (Altschul et al., J. Mol. Bio. 215: 403, 1990) and known RNase P polypeptide sequences from *E. coli* (gram-negative) and *B. subtilis* (gram-positive) as "query" sequences. Given that the largest number of known RNase P protein subunit sequences correspond to sequences from gram-negative and gram-positive bacteria, "query" sequences from both bacterial groups were used in the search to ensure that all novel sequences having homology to known RNase P sequences would be identified.

BLAST searches of genomic databases for potential RNase P homologues were performed in the following URLs: http://www.ncbi.nlm.nih.gov/BLAST/ unfinishedgenome.html; and http://www.tigr.org/cgi-bin/ BlastSearch/blast.cgi.

The BLAST program only considered hits with a P-value of less than or equal to $10^{-5}$ to ensure that random hits were not sampled.

The above-described searches often yielded multiple hits in the genomic databases. To identify which sequences were genuine RNase P protein subunits, we determined whether the sequences also contained an RNase P consensus sequence, which we defined as a sequence that, upon alignment with known RNase P sequences using the ClustalW program, conserves at least nine of the following twenty amino acids in the *E. coli* RNase P protein sequence: R11, L12, F18, R46, G48, V51, K53, K54, A59, V60, R62, N63, K66, R67, R70, L80, D84, V86, L101, and L105. Preferred sequences contained at least thirteen out of the twenty residues and/or had at least seven of the following amino acid subset: F18, R46, K53, A59, R62, N63, K66, R67, and R70.

This RNase P consensus sequence was derived as follows. We aligned the sequences of the known bacterial RNase P protein subunits using the ClustalW alignment program (Thompson et al., supra) (see FIG. 1, the previously known RNase P sequences were obtained from the RNase P database; www.jwbrown.mbio.ncsu.edu/rnasp/home.html.) This ClustalW alignment was then manually refined to align highly conserved RNase P hydrophobic and basic residues that had been demonstrated by mutation studies to be important for RNase P catalytic function (Gopalan et al., J. Mol. Biol. 267: 818, 1997). The spacing between the conserved residues, as well as the identity of the individual residues, appears critical to RNase P function.

Twenty amino acids were identified as highly conserved (shown as the shaded residues in FIG. 1). The percent of RNase P sequences which conserve each of the shaded residues is shown below the sequence information as percent identity. Based upon these known sequences, we determined that a polypeptide identified by our above-described RNase P BLAST search contained an RNase P consensus sequence and was a genuine RNase P protein subunit if it contained at least nine of the above-described twenty amino acids. Preferred polypeptides have a consensus sequence with at least 13 of the amino acids and/or conserve at least seven of the following subset of amino acids: F18, R46, K53, A59, R62, N63, K66, R67, and R70. This subset of amino acids is preferred because it has been identified as playing a significant role in RNase P function through mutation studies (Gopalan et al., J. Mol. Biol. 267: 818 1997) and the determination of the RNase P three dimensional structure (Stains et al., Science 280: 752, 1998). The three dimensional structure reveals that all of the residues that make up the above-described nine amino acid subset are proximal to each other in the tertiary structure of the protein, despite the distance between some of the residues in the primary structure.

2. RNase P Protein Amino Acid and Nucleic Acid Sequences

The novel RNase P proteins of the invention, and the nucleic acid sequences which encode the proteins, are derived from the following bacterial species: *Streptococcus mutans* UAB159; *Klebsiella pneumoniae* M6H 78578; *Salmonella paratyphi* A (ATCC 9150); *Pseudomonas aeruginosa* PAO1; *Corynebacterium diphtheriae*; *Chlamydia trachomatis* MoPn; *Vibrio cholerae* Serotype 01, Biotype El Tor, Strain N16961; *Neisseria gonorrhoea* FA 1090; *Neisseria meningitidis* Serogroup A, Strain Z2491; *Streptococcus pyogenes* M1; *Bordetella pertussis* Tohama I; *Porphyromonas gingivalis* W83; *Streptococcus pneumoniae* Type 4; *Clostridium difficile* 630; *Camphylobacter jejuni* NCTC; *Bacillus anthracis* Ames; *Mycobacterium avium* 104. *Staphylococcus aureus* NCTC 8325; *Staplylococcus aureus* COL; *Pasteurella multocida* PM70; *Haemophilus ducreyi* strain 35000HP; *Chlamydia muridarum*; *Chlamydophila psittaci*; *Treponema denticola*; *Enterococcus faecalis*; *Legionella pneumophila*; *Staphylococcus epidermis*; *Mycobacterium smegmatis*; *Burkholderia pseudomallei*; and *Ureaplasma urealyticum*. The sequences are shown in FIGS. 2 and 3.

All of the novel RNase P protein sequences were identified by the above-described BLAST search. The alignment of these sequences with the known RNase P sequences is also shown in FIG. 1. This alignment demonstrates that the amino acid sequences of the invention all contain RNase P consensus sequences. Therefore, these polypeptides are genuine RNase P proteins.

The RNase P identification is further supported by the protein structure of the polypeptides of the invention, as determined by SWISS-MODEL. The SWISS MODEL is an automated protein modelling server running at the Glaxo Wellcome Experimental Research in Geneva, Switzerland (http://www.expasy.ch/swissmod/swiss.model). The polypeptide sequences of the invention were readily folded (at least in part) into the tertiary structure of the *B. subtilis* RNase P protein subunit (Stams et al., supra). It is noteworthy that conserved residues in the newly identified sequences are modeled into positions which are spatially and structurally identical to the RNase P protein subunit of *B. subtilis*.

Further support for the RNase P identification is as follows. Using the above-described BLAST search and consensus sequence determination, we independently identified the sequence for an RNase P protein subunit from the genomic database of *Staphylococcus aureus* (*S. aureus*). Although this sequence had been previously identified as an RNase P protein subunit and its RNase P activity had been confirmed by assay (EPA 0 811 688 A2), our independent discovery of this RNase P sequence provides proof of principle that our method of searching for RNase P protein subunits predictably identifies polypeptides that have RNase P activity.

The invention features purified or isolated RNase P protein subunits. As used herein, both "protein" and "polypeptide" mean any chain of amino acids, regardless of length or post-translational modification (e.g., glycosylation or phosphorylation). Thus, the term RNase P protein subunit includes full-length, naturally-occurring RNase P proteins, preproteins, and proproteins, as well as recombinantly or synthetically produced polypeptides that correspond to full-length, naturally-occurring RNase P proteins or to particular domains or portions of naturally-occurring proteins. These proteins are produced using standard techniques (see, e.g., Ausubel et al., *Current Protocols in Molecular Biology*, John Wiley & Sons, New York, 1995; Pouwels et al., *Cloning Vectors: A Laboratory Manual*, 1985 (1987 Suppl.); and Sambrook et al., *Molecular Cloning, A Laboratory Manual*, $2^{nd}$ ed., Cold Spring Harbor Laboratory Press, Cold Spring Harbor, N.Y., 1989).

Preferred RNase P proteins include a sequence substantially identical to all or a portion of a naturally occurring RNase P protein subunit, e.g., including all or a portion of any of the sequences shown in FIG. 2 (SEQ ID NOS: 20–38) and FIG. 3 (SEQ ID NOS; 50–60).

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Preferred polypeptides are those which are soluble under normal physiological conditions. Also within the invention are soluble fusion proteins in which a full-length or sub-fragment of RNase P protein (e.g., one or more domains) is fused to an unrelated protein or polypeptide (i.e., a fusion partner) to create a fusion protein.

Structurally related RNase P polypeptides of the invention include, but are not limited to, polypeptides with additions or substitutions of amino acid residues within the amino acid sequence encoded by the RNase P nucleic acid sequences described herein; these changes result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, -cysteine, tyrosine, asparagine, and glutamine; positively charged (basic) amino acids include arginine, lysine, and histidine; and negatively charged (acidic) amino acids include aspartic acid and glutamic acid.

Preferred RNase P polypeptides and variants have 20%, 50%, 75%, 90%, or even 100% or more of the activity of one of the bacterial RNase P proteins of SEQ ID NOS: 20–38 shown in FIG. 2, or of SEQ ID NOS: 50–60 shown in FIG. 3. Such comparisons are generally based on equal concentrations of the molecules being compared. The comparison can also be based on the amount of protein or polypeptide required to reach the maximal activation obtainable.

In general, RNase P proteins according to the invention can be produced by transformation (transfection, transduction, or infection) of a host cell with all or part of a RNase P-encoding nucleic acid sequence of the present invention in a suitable expression vehicle. Such expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene, LaJolla, Calif.).

Those skilled in the field of molecular biology will understand that any of a wide variety of expression systems can be used to provide the recombinant protein (see, e.g., Ausubel et al., *Current Protocols in Molecular Biology*, John Wiley & Sons, New York, 1995; Pouwels et al., *Cloning Vectors: A Laboratory Manual*, 1985 (1987 Suppl.); and Sambrook et al., *Molecular Cloning, A Laboratory Manual*, $2^{nd}$ ed., Cold Spring Harbor Laboratory Press, Cold Spring Harbor, N.Y., 1989). The precise host cell used is not critical to the invention. The RNase P protein can be produced in a prokaryotic host (e.g., *E. coli* or *B. subtilis*) or in a eukaryotic host (e.g., Saccharomyces or Pichia; mammalian cells, e.g., COS, NIH 3T3 CHO, BHK, 293, or HeLa cells; or insect cells; or plant cells).

The host cells harboring the expression vehicle can be cultured in conventional nutrient media adapted as needed for activation of a chosen gene, repression of a chosen gene, selection of transformants, or amplification of a chosen gene.

RNase P proteins can be produced as fusion proteins. For example, the expression vector pUR278 (Ruther et al., EMBO J. 2: 1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

The invention also features the isolated nucleic acid sequences of SEQ ID NOS: 1–19 shown in FIG. 2 and SEQ ID NOS: 39–49 shown in FIG. 3, and nucleic acid sequences that encode one or more portions or domains of an RNase P protein subunit, including but not limited to the $\alpha1$, $\alpha2$, $\alpha3$, $\beta1$, $\beta2$, $\beta3$, and $\beta4$ portions of the protein.

Preferred nucleic acids encode polypeptides that are soluble under normal physiological conditions. Also within the invention are nucleic acids encoding fusion proteins in which the whole RNase P protein or a sub-fragment is fused to an unrelated protein or polypeptide (e.g., a marker polypeptide or a fusion partner) to create a fusion protein. For example, the polypeptide can be fused to a hexa-histidine tag to facilitate purification of bacterially expressed protein, or to a hemagglutinin tag to facilitate purification of protein expressed in eukaryotic cells.

The fusion partner can be, for example, a polypeptide which facilitates secretion, e.g., a secretory sequence. Such a fused protein is typically referred to as a preprotein. The secretory sequence can be cleaved by the host cell to form the mature protein. Also within the invention are nucleic acids that encode a mature RNase P protein fused to a polypeptide sequence to produce an inactive proprotein. Proproteins can be converted into the active form of the protein by removal of the inactivating sequence.

The nucleic acids of the invention further include sequences that hybridize, e.g., under high stringency hybridization conditions (as defined herein), to all or a portion of the nucleic sequence of any one of SEQ ID NOS: 1–19 or 39–49, or any of their complements. As used herein, high stringency conditions include hybridizing at 68° C. in 5×SSC/5×Denhardt solution/1.0% SDS, or in 0.5 M NaHPO4 (pH 7.2)/1 mM EDTA/7% SDS, or in 50% formamide/0.25 M NaHPO4 (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO4 (pH 7.2)/1 mM EDTA/5% SDS at 50° C., or in 40 mM NaHPO4 (ph 7.2)/1 mM EDTA/1% SDS at 50° C. The parameters of salt concentration and temperature can be varied to achieve the desired level of identity between the probe and the target nucleic acid. Further guidance regarding hybridizing conditions is provided, for example, in Sambrook et al., *Molecular Cloning, A Laboratory Manual*, Cold Springs Harbor Press, NY, 1989; Ausubel et al., *Current Protocols in Molecular Biology*, John Wiley & Sons, NY, 1995).

The hybridizing portion of the hybridizing nucleic acids are preferably 20, 30, 50, or 70 bases long. Preferably, the hybridizing portion of the hybridizing nucleic acid is 80%, more preferably 95%, or even 98% identical, to the sequence of a portion or all of a nucleic acid encoding an RNase P protein subunit. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by a naturally-occurring RNase P protein subunit. Such biological activity can be determined by functional RNase P assay as described herein.

Hybridizing nucleic acids can be additional splice variants of the RNase P protein gene. Thus, they may encode a protein which is shorter or longer than the different forms of RNase P described herein. Hybridizing nucleic acids may also encode proteins that are related to RNase P (e.g., proteins encoded by genes which include a portion having a relatively high degree of identity to the RNase P genes described herein).

The invention also features vectors and plasmids that include a nucleic acid of the invention which is operably linked to a transcription and/or translation sequence to enable expression, e.g., expression vectors.

2. RNase P Antibodies

The bacterial RNase P proteins and polypeptides (or immunogenic fragments or analogs) can be used to raise antibodies useful in the invention, and such polypeptides can be produced by recombinant or peptide synthetic techniques (see, e.g., Ausubel et al., *Current Protocols in Molecular Biology*, John Wiley & Sons, New York, 1995). In general, the peptides can be coupled to a carrier protein, such as KLH, mixed with an adjuvant, and injected into a host mammal. Antibodies can be purified by peptide antigen affinity chromatography.

In particular, various host animals can be immunized by injection with an RNase P protein or polypeptide. Host animals include rabbits, mice, guinea pigs, and rats. Various adjuvants can be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Antibodies within the invention include polyclonal antibodies, humanized or chimeric antibodies, single chain antibodies, Fab fragments, F(ab')$_2$ fragments, molecules produced using a Fab expression library, and monoclonal antibodies.

Monoclonal antibodies can be prepared using the RNase P proteins described above and standard hybridoma technology (see, e.g., Kohler et al., Nature 256: 495, 1975; Kohler et al., Eur. J. Immunol. 6: 511, 1976; Hammerling et al., In *Monoclonal Antibodies and T Cell Hybridomas*, Elsevier, N.Y., 1981; and Ausubel et al., *Current Protocols in Molecular Biology*, John Wiley & Sons, New York, 1995).

In particular, monoclonal antibodies can be obtained by any technique that provides for the production of antibody molecules by continuous cell lines in culture, such as described in Kohler et al., Nature 256: 495, 1975, and U.S. Pat. No. 4,376,110; the human B-cell hybridoma technique (Kosber et al., Immunology Today 4: 72, 1983; and Cole et al., Proc. Natl. Acad. Sci. USA 80: 2026, 1983), and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridoma producing the mAb of this invention can be cultivated in vitro or in vivo. The ability to produce high titers of mAbs in vivo makes this the presently preferred method of production.

Once produced, polyclonal or monoclonal antibodies are tested for specific RNase P recognition by Western blot or immunoprecipitation analysis by standard methods, for example, as described in Ausubel et al., *Current Protocols in Molecular Biology*, John Wiley & Sons, New York, 1995. Preferred antibodies specifically bind the RNase P proteins of the invention.

Preferably, the antibodies of the invention are produced using fragments of the RNase P protein which lie outside highly conserved regions and appear likely to be antigenic, by criteria such as high frequency of charged residues. In one specific example, such fragments are generated by standard techniques of PCR, and are then cloned into the PGEX expression vector. Fusion proteins are expressed in *E. coli* and purified using a glutathione agarose affinity matrix (Ausubel, et al., *Current Protocols in Molecular Biology*, John Wiley & Sons, New York, 1995).

Another aspect of the invention features a method for detecting an RNase P protein. This method includes: contacting an antibody that specifically binds an RNase P protein of the present invention to a biological sample under conditions that allow the formation of RNase P-antibody complexes; and detecting the complexes, if any, as an indication of the presence of RNase P protein in the biological sample.

The following examples are to illustrate the invention. They are not meant to limit the invention in any way.

EXAMPLE 1

Screening for Antibacterial Agents

The rnpA genes encoding the RNase P proteins or protein subfragments of the invention are amplified from genomic DNA by. established PCR methods. The amplified DNA sequences that encode the RNase P protein genes are subcloned into expression plasmids, which contain fusion sequences allowing the subcloned gene to be expressed in a transformed or transfected host cell as a "tagged" fusion protein. *E. coli* cells are transformed with the plasmid DNA, protein expression is induced, and the overexpressed fusion protein is isolated by affinity purification according to established protocols.

Each of the purified RNase P proteins is combined with a renatured cognate RNase P RNA subunit from the same, or a different, bacterial organism, under conditions that reconstitute enzymatic activity. It is possible to reconstitute a functional RNase P holoenzyme using a protein subunit and an RNA subunit from different species (e.g., *B. subtilis, E. coli*, or *S. aureus*). The conditions for reconstitution include heat. denaturing the RNA subunit then slowly cooling in a physiologically similar buffer. A buffer for folding the RNA component of RNase P is 10–50 mM Tris-HCl/MOPS/ HEPES (pH=7.0–8.0), 25–500 mM KCl/NaCl/NH$_4$ and 1–25 mM MgCl$_2$. The RNA is heated to 65° C. for 5 minutes, 55° C. for minutes, and 37° C. for 5 minutes. The protein is then added along with 1–10 mM DTT and the incubation is optionally continued at 37° C. for 5 minutes. Similar heating protocols known in the art may also be used. The protein is then incubated briefly with the renatured RNA to reconstitute holoenzyme activity.

The RNase P substrates used in the assay can be labeled. Examples of labeled nucleotides that can be incorporated into the RNA substrates include BrdUrd (Hoy and Schimke, Mutation Research 290: 217, 1993), BrUTP (Wansick et al., J. Cell Biology 122:283, 1993) and nucleotides modified with biotin (Langer et al., Proc. Natl. Acad. Sci. USA 78: 6633, 1981) or with suitable haptens such as digoxygenin (Kerhof, Anal. Biochem. 205: 359, 1992). Suitable fluorescence-labeled nucleotides are Fluorescein-isothiocyanate-dUTP, Cyanine-3-dUTP and Cyanine-5-dUTP (Yu et al., Nucleic Acids Res. 22:3226, 1994). A preferred nucleotide analog label for RNA molecules is Biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

The amplified rnpA genes may also be cloned into expression vectors not containing encoded fusion tag sequences, but still containing an inducible promoter. After induction, the overexpressed protein can be purified essentially by the protocol for purification of *E. coli* RNaseP protein (Baer et al., 1990).

Examples of RNA substrates that can be used to measure RNase P enzymatic activity include the full-length substrate ptRNA$^{Tyr}$ (pTyr) (Altman and Kirsebom, *The RNA World, 2$^{nd}$ Ed.*, Cold Spring Harbor Laboratory Press, Cold Spring Harbor, N.Y., 1999), and ptRNA$^{Gln}$ (pGln), an 85-mer from the cyanobacterium Synechocystis (Pascual and Vioque, Proc. Natl. Acad. Sci. USA 96: 6672, 1999) or a substrate obtained from the homologous bacteria.

A modified ptRNA$^{Gln}$ substrate can also be used, in which the 5' end is fluorescently tagged in order to monitor hydrolysis using fluorescence spectroscopy. Given that the chemical synthesis of an 85-mer with a fluorescent tag is technically impractical, and the fluorescent modification enzymatically synthesized RNA is difficult, the preferred method of synthesizing a fluorescently tagged pGln is conducted with the following two steps: a 5' fluorescently modified 26-nucleotide fragment is chemically synthesized and annealed to a 3' 59-nucleotide fragment that has been enzymatically synthesized. These two fragments, when annealed, form a full-length pGln substrate. The unligated junction between the two fragments occurs in the D-loop, a region that is not required for function by the RNase P holoenzyme.

In addition, substrates that contain only the minimally required structural elements for recognition by the enzyme can also be utilized for this reaction, although the Km values for these substrate fragments are usually much higher than the above-described full-length substrates. One example of a substrate fragment is p10AT1, a 45-mer that contains a 10-nucleotide 5' leader sequence, an extended 12-base pair stem which is made up of the aminoacyl acceptor stem, a T-stem, and a single loop. The Km for hydrolysis reactions using this simplified substrate fragment rises to greater than 1 µM (McClain et al., 1987). Therefore, while the substrate fragment is easier to construct, it requires a higher concentration in an enzymatic assay.

The progress of the RNase P-mediated hydrolysis reaction is monitored, for example, by fluorescence spectroscopy. For example, a fluorescence polarization assay for RNase P activity is conducted by labeling the 5' end of the substrate, for example, the 45-mer (p10AT1) or the 85-mer (pGln) substrate, with an appropriate fluorophore. Given that compounds in screening libraries often interfere with fluorescence measurements in the blue to yellow region of the spectrum, preferred fluorophores emit light in the red region of the spectrum (e.g., TAMRA (Molecular Probes, OR) and Cy3 labeled nucleotide (Dharmacon Research, CO.) Samples of the RNase P holoenzyme and the RNase P substrate are mixed, incubated, and measured for spectrophotometric polarization. When the substrate is cleaved by the RNase P holoenzyme, the 10-nucleotide 5'-leader sequence is released, which leads to a substantial change in the fluorescence polarization in the sample. (Campbell, I.D. & Dwed., R. A. pp. 91–125 The Benjamin/Cummings Publishing Company, Menlo Park, Calif. (1984); Lakowicz, J. R., Plenum Press, NY (1983)).

The preferred reaction buffer contains 50 mM Tris-HCl (pH 7.5), 100 mM ammonium chloride and 10 mM magnesium chloride. Concentrations of 10–100 mM, 25–500 mM and 1–100 mM of the above, respectively, can be substituted, as can other buffering agents such as MOPS or HEPES, or other monovalent cations, such as sodium or potassium. When the assay is run in either 96 or 384-well polystyrene or polypropylene assay plates, there is a very significant decrease in the fluorescence intensity and polarization of the annealed substrate over time in the absence of enzyme. Various conditions have been tested to prevent the loss of signal with time. The preferred conditions include addition of 10–40 µg/ml carbonic anhydrase and 10–100, µg/ml polyC to the buffer. Other materials, such as, 0.5–5% glycerol, 10–100 µg/ml hen egg lysozyme, 10–50 µg/mL tRNA, 1–10 mM DTT, or 2–10 mM DTT can also be added to the buffer to prevent some loss of signal.

The RNase P hydrolysis rate can also be monitored using a radiolabeled substrate, performing a surface proximity assay (SPA), and measuring hydrolysis by scintillation counting. For example, the substrate is anchored to the surface of the assay plate via a biotin-streptavidin interaction between a biotinylated nucleotide in the anticodon loop and a streptavidin matrix on the plate. The substrate is also $^{33}$P-labeled at the 5' end. Using this method, RNase P-mediated hydrolysis of the 5' leader sequence results in decreased scintillation due to reduced proximity of the radiolabel to the scintillation-coated plate. (Brown et al., FlashPlate Technology, in J. P. Devlin (Ed.), Marcel Dekker, Inc. NY pp. 317–328.)

A bipartite substrate for RNase P, consisting of a 5'-end Cy3 labeled 26mer and an in vitro T7-polymerase transcribed 59mer is preferred for screening. The 26mer consists of the first 26 contiguous nucleotides of the pre-tRNA substrate including the 10-nucleotide leader sequence. The two RNA fragments are annealed together under appropriate conditions of stoichiometry (59mer in 20 to 100% excess) and temperature in a buffer system consisting of 50 mM Tris-HCl (pH 7.5), 100 mM ammonium chloride, and 10 mM magnesium chloride. Briefly, the two RNA fragments are mixed together and heated to between 65° C. and 80° C. for about 5 minutes and then slowly cooled to room temperature.

In addition, the RNase P enzyme activity can also be measured using standard techniques described in the literature (see, e.g., Altman and Kirsebom, Ribonuclease P, *The RNA World*, 2$^{nd}$ Ed., Cold Spring Harbor Laboratory Press, Cold Spring Harbor, N.Y., 1999; Pascual and Vioque, Proc. Natl. Acad. Sci. 96: 6672, 1999; Geurrier-Takada et al., Cell 35: 849, 1983; Tallsjö and Kirsebom, Nucleic Acids Research 21: 51, 1993; Peck-Miller and Altman, J. Mol. Biol. 221: 1, 1991; Gopalan et al., J. Mol. Biol. 267: 818, 1997; and WO 99/11653).

To screen for compounds that inhibit the activity of the RNase P holoenzymes of the present invention, compounds are added to a final concentration of 10 µM before the addition of substrate to the sample. A compound is determined to be an inhibitor if it significantly reduces RNase P hydrolysis as compared to the compound-free control sample. Ideally, the compounds identified as inhibitors selectively inhibit one of the RNase P holoenzymes of the invention without affecting other RNase P holoenzymes. Such inhibitors have the advantage of providing a selective antibacterial treatment that reduces the adverse side effects associated with killing nonpathogenic bacteria. Use of such selective inhibitors also reduces the risk of producing a wide range of resistant bacterial strains.

EXAMPLE 2
High Throughput Screening for Antibacterial Agents

The following assay is used for high throughput screening of antibacterial agents.

The assay buffer (PA buffer) for high throughput screening contains 50 mM Tris-HCl, pH 7.5; 100 mM $NH_4Cl_2$; 10 mM $MgCl_2$; 1 mM DTT; and 1 mg/ml BSA. One mM DTT is used in this buffer to keep the C5 protein (see below) disulfide bonds intact, and BSA is used to block non-specific binding of assay components to the wells of the polystyrene assay plates. Total volume of the assay is 50 µl.

Compounds to be tested as antibacterial agents in this assay are stored in 384-well polypropylene plates as 2 µl aliquots of a 1 mM DMSO solution. No-compound control wells contain 2 µl of DMSO only and are diluted in like manner. The compounds are diluted in the plates with assay buffer to a 40 µM concentration and are assessed at a final concentration of 10 µM. A 12.5 µl aliquot of each compound dilution is transferred to two black untreated Costar 384 well polystyrene plates. One of the plates receives the RNase P enzyme and substrate and constitutes the screening assay plate. The other plate receives PA buffer and Stop solutions without TAMRA-labeled oligonucleotide and constitutes the compound background plate.

The enzyme used in the assay is *N. Gonorrhea* RNase P and is composed of an RNA subunit designated M1, and a protein subunit designated C5. The M1 component is added, at a final concentration of 0.1 nM, to the wells of the screening assay plate containing diluted compounds and those wells designated as plus-enzyme control wells that contain diluted DMSO only. Wells designated as minus-enzyme controls receive an equivalent volume of PA buffer only.

The C5 enzyme component is added, to a final concentration of 0.5 nM, to the wells of the screening assay plate containing diluted compounds and those wells designated as plus-enzyme control wells that contain diluted DMSO only. Wells designated as minus-enzyme controls receive an equivalent volume of PA buffer only.

The substrate used is ptRNA$^{Gln}$ (pGln), an 85-mer RNA derived from the cyanobacterium Synechocystis, produced via in vitro transcription from a DNA template. The substrate is added in assay buffer for a final concentration of 40 nM.

In this assay, none of the reagents need to be re-natured before addition to the assay, and in fact, this type of renaturation step is detrimental to the activity of the enzyme.

The cleavage reaction is allowed to proceed for 30 minutes and is stopped by the addition of 50 µl of 100 mM EDTA, diluted in PA buffer containing 150 mM NaCl and 15 mM $Na_3$ Citrate, pH 7.0. The stop buffer also contains a 5'-TAMRA-labeled 17-nucleotide DNA oligonucleotide (TAMRA-17mer) that has a sequence complementary to the 10 nucleotide leader sequence of the substrate plus the subsequent 7 nucleotides of the aminoacyl acceptor stem. The TAMRA-17mer is added to a final concentration of 5 nM. The progress of the RNase P-mediated cleavage reaction is assessed by measuring the fluorescence polarization level of the TAMRA moiety hybridized to the cleaved leader or the intact substrate. The hybridization process is somewhat slow and the components need be incubated for at least two hours to achieve maximal signal differentials.

It will be understood that the above-described high throughput screening assay can be used with any RNase P polypeptide. In addition, the oligonucleotide used in the fluorescence polarization assay may be labeled with any number of different tags, as described herein.

EXAMPLE 3
Compounds for Use in Screening for Antibacterial Agents

In general, extracts, compounds, or chemical libraries that can be used in screening assays are known in the art. Examples of such extracts or compounds include, but are not limited to, extracts based on plant, fungal, prokaryotic, or animal sources, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Libraries of genomic DNA or cDNA may be generated by standard techniques (see, e.g., Ausubel et al., supra) and are also commercially available (Clontech Laboratories Inc., Palo Alto, Calif.).

Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceanographics Institute (Ft. Pierce, Fl.), and PharmaMar, U.S.A. (Cambridge, Mass.). In addition, natural and synthetically produced libraries are produced, if desired, according to methods known in the art, e.g., by standard extraction and fractionation methods.

When a crude extract is found to modulate an RNase P holoenzyme activity, further fractionation of the positive lead extract is necessary to isolate chemical constituents responsible for the modulation. Thus, the goal of the extraction, fractionation, and purification process is the characterization and identification of a chemical entity within the crude extract having the modulating activities. The same assays described herein for the detection of inhibitors in mixtures of compounds can be used to purify the active component and to test derivatives thereof Methods of fractionation and purification of such heterogenous extracts are known in the art. If desired, compounds shown to be useful agents for treatment are chemically modified according to methods known in the art.

Compounds which modulate an RNase P holoenzyme activity may be administered by any appropriate route for treatment or prevention of a disease or condition associated with a bacterial infection. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (19th ed., ed. A. R. Gennaro A R., 1995, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The formulations can be administered to human patients in therapeutically effective amounts (e.g., amounts which prevent, eliminate, or reduce a pathological condition) to provide therapy for a disease or condition associated with infection. Typical dose ranges are from about 0.1 $\mu$g/kg to about 1 g/kg of body weight per day. The preferred dosage of drug to be administered is likely to depend on such variables as the type and extent of the disorder, the overall health status of the particular patient, the formulation of the compound excipients, and its route of administration.

Other Embodiments

All publications and patent applications mentioned in this specification are herein incorporated by reference.

While the invention has been described in connection with specific embodiments, it will be understood that it is capable of fierier modifications. Therefore, this application is intended to cover any variations, uses, or adaptations of the invention that follow, in general, the principles of the invention, including departures from the present disclosure that come within known or customary practice within the art. Other embodiments are within the claims.

What is claimed is:

1. An isolated polypeptide comprising an RNase P consensus sequence, said polypeptide comprising the amino acid sequence of SEQ ID NO: 55, wherein said polypeptide has RNase P protein activity.

2. A method of identifying an antibiotic agent, said method comprising:
   i) contacting an RNase P holoenzyme comprising the polypeptide of claim 1 with an RNase P substrate in the presence and in the absence of a compound; and
   ii) measuring the enzymatic activity of said holoenzyme;
   wherein a compound is identified as an antibiotic agent if said compound produces a detectable decrease in said RNase P enzymatic activity as compared to activity in the absence of said compound.

3. The method of claim 2, wherein said activity is measured by fluorescence spectroscopy.

4. The method of claim 3, wherein said RNase P substrate is fluorescently tagged ptRNA$^{Gln}$.

5. The method of claim 3, wherein said contacting is carried out in a buffer comprising 10–40 μg/ml carbonic anhydrase and 10–100 μg/ml polyC.

6. The method of claim 5, wherein said buffer further comprises at least one of the following:
   0.5–5% glycerol;
   10–100 μg/ml hen egg lysozyme;
   10–50 μg/ml tRNA; or
   1–10 mM DTT.

7. The method of claim 2, wherein said polypeptide, when combined with an RNA subunit to form an RNase P holoenzyme, has at least 20% of the enzymatic activity of an E. coli or B. subtilis RNase P holoenzyme.

8. A method of identifying an antibiotic agent, said method comprising:
   i) contacting an RNase P holoenzyme comprising an RNase P polypeptide and having RNase P protein activity with an RNase P substrate in the presence and in the absence of a compound, wherein said RNase P polypeptide comprises the sequence set forth in SEQ ID NO: 55; and
   iii) measuring the enzymatic activity of said holoenzyme, said measuring comprising determining the fluorescence polarization level of a fluorescently tagged oligonucleotide that hybridizes to either the cleaved or intact form of said substrate; wherein said compound is identified as an antibiotic agent if said compound produces a detectable decrease in said RNase P enzymatic activity as compared to activity in the absence of said compound.

9. The method of claim 8, wherein said RNase P substrate is ptRNA$^{Gln}$.

10. The method of claim 8, wherein said polypeptide, when combined with an RNA subunit to form an RNase P holoenzyme, has at least 20% of the enzymatic activity of an E. coli or B. subtilis RNase P holoenzyme.

11. A method of identifying a polypeptide with an RNase P polypeptide consensus sequence, said method comprising the steps of:
   (a) identifying a polypeptide that has sequence identity to a known RNase P polypeptide; and
   (b) determining if said identified polypeptide of step (a) conserves at least nine of the following twenty amino acids in the E. coli RNase P protein sequence: R11, L12, F18, R46, G48, V51, K53, K54, A59, V60, R62, N63, K66, R67, R70, L80, D84, V86, L101, and L105, wherein the numbering of said twenty amino acids refers to that of *E. coli* RNase P, and wherein a polypeptide that does conserve at least nine of said twenty amino acids in the *E. coli* RNase P protein sequence is a polypeptide with an RNase P consensus sequence.

12. The method of claim 11, wherein said polypeptide comprises the following twenty amino acids: R11, L12, F18, R46, G48, V51, K53, K54, A59, V60, R62, N63, K66, R67, R70, L80, D84, V86, L101, and L105, wherein the numbering refers to the position of the amino acid in the sequence of *E. coli* RNase P.

13. The method of claim 11, wherein said identified polypeptide, when combined with an RNA subunit to form an RNase P holoenzyme, has at least 20% of the enzymatic activity of an *E. coli* or *B. subtilis* RNase P holoenzyme.

14. The method of claim 11, wherein said identified polypeptide is a bacterial polypeptide.

15. The method of claim 14, wherein said identified polypeptide is not a polypeptide from one of the following organisms: *Coxiella burnetii* (None Mile) U10529, *Rickettsia prowazekii* (Madrid E) AJ235272, *Neisseria meningitidis* (Z2491) AL162753, *Neisseria meningitidis* (MC58) AE002540, *Buchnera aphidocola* M80817, *Buchnera aphidocola* (SGS) AF008210, Buchnera sp. (APS) AP000398, *Haemophilus influenza* (RD KW20) U32848, *Escherichia coli* M11056, *Escherichia coli* (K-12) AE000394, *Proteus mirabilis* M58352, *Pseudomonas aeruginosa* (PAO1) AE004968, *Pseudomonas putida* P25752, *Salmonella typhi* (CT18), *Yersinia pestis* (Orientalis), *Xyelella fastidiosa* AE004083, *Campylobacter jejuni* (NCTC 11168) AL139076, *Helicobacter pylori* (26695) AE000645, *Helicobacter pylori* (J99) AE001557, *Micrococcus luteus* (S66) U64884, *Mycobacterium avium* (104) AF222789, *Mycobacterium bovis* (AF2122/97), *Mycobacterium leprae* (Lortist 6) L39923, *Mycobacterium tuberculosis* (H37Rv) AL021426 X92504, *Streptomyces bikiniensis* (Zorbonenis) M83112, *Streptomyces coelicolor* (A3(2)) M82836 AL049826 AF031590, *Bacillus halodurans* (C-125) AB013492, *Bacillus subtilis* (168) X62539 AL009126, *Mycoplasma capricolum* (mcs5) P14982, *Mycoplasma genitalium* (G-37) U39713, *Mycoplasma pneumoniae* (M-129) U00089, *Staphylococcus aureus* (ISP3) AF135268, *Ureaplasma urealyticum* (3/1) AE002158, Pseudanabaena sp. (PCC6903) AJ000513 Synechocystis sp. (PCC6803) X81989, *Borrellia burgdorferi* (212) Z12166, *Borrellia burgdorferi* (B31) AE000783, *Treponema pallidum* (Nichols) P50069, *Chlamydia trachomatis* (serovar D) AE001351, *Chlamydia muridarum* (trachomatis MoPn) AE002160, *Chlamydophila pneumoniae* (CWL 029) AE001673, *Chlamydophila pneumoniae* (AR39) AE002251, *Deinococcus radiodurans* (R1) AE002049, *Thermotoga maritima* (MSB8) AAD36531, *B. burgdorferi*, *B. burgdorferi*-partial, *C. burnetii*, *C. pneumoniae*-2, *C. trachomatis*, *H. influenza*, *H. pylori*-48, *M. leprae*, *M. luteus*, *M. tuberculosis*-2, *M. bovis*, Pseudanabaena-6903, *R. prowazeki*, *S. bikiniensis*, Synechocystis 6803, *Staphylococcus aureus*, and *S. pneumoniae*.

* * * * *

SEQUENCE LISTING

<160> NUMBER OF SEQ ID NOS: 60

<210> SEQ ID NO 1
<211> LENGTH: 417
<212> TYPE: DNA
<213> ORGANISM: Streptococcus mutans

<400> SEQUENCE: 1

```
agattttgg ctttttctca ttttatgata taatagtgat aatttaaata ttggagtcat      60
gttttgaaaa aagcctatcg cgttaaaagt gataaagatt ttcaggcaat ttttactgaa     120
ggacgaagtg ttgccaatcg gaaatttgtt gtctatagtt tagaaaaaga tcaaagtcac     180
tatcgtgttg gactttcagt tggaaaaaga ttaggaaatg ctgtcgttag aaatgcgatt     240
aaacgaaaat tgcgccatgt ccttatggaa cttggtcctt atttaggcac tcaagatttt     300
gttgttattg ctagaaaagg tgttgaggaa cttgattata gcacgatgaa aaaaaatctg     360
gttcatgttt taaaactggc taaactgtat caggaaggat ctattcgtga aaaagaa       417
```

<210> SEQ ID NO 2
<211> LENGTH: 477
<212> TYPE: DNA
<213> ORGANISM: Klebsiella pneumoniae

<400> SEQUENCE: 2

```
cgtcgtcgtg ctaaaggccg cgctcgtctg accgtttcca agtaataaag ctaaccctgc      60
gtggttaagc tcgcatttcc cagggagtta cgcttgttaa ctcccagtca tttcactttc     120
gtcttccagc agccacaacg ggctggcacg ccgcaaatca ccatcctcgg ccgcctgaat     180
tcgctggggc atccccgcat cggtctcacc gtcgccaaga aaaacgtgaa acgcgcacat     240
gaacgcaatc ggattaaacg tctgacgcgt gaaagttttc gtttgcgtca acatgaactc     300
```

-continued

```
ccgccaatgg atttcgtggt ggtggcgaaa agaggggttg ccgacctcga taaccgtgct    360
ctctcggaag cgttggaaaa attatggcgc cgccattgtc gcctggctcg cgggtcctga    420
tcggcctgat tcgagtttat cagcgcctga ttagtccgct actcgggccg cattgtc      477
```

<210> SEQ ID NO 3
<211> LENGTH: 455
<212> TYPE: DNA
<213> ORGANISM: Salmonella paratyphi

<400> SEQUENCE: 3

```
ctgaccgttt ccaagtaata aagctaaccc ctgagtggtt aagctcgcat ttcccaggga    60
gttacgtttg ttaactcccg ctcatttcac attcgtcttc cagcaacctc aacgggctgc   120
acgccgcaaa tcaccatcct cggccgcctg aattcgctgg gcatccccg tatcggtctt    180 accgtcgcca agaaaaatgt tcgacgtgcg catgaacgca accggattaa acgtctgacg    240
cgtgaaagct tccgtctgcg ccagcatgaa cttcctgcaa tggatttcgt ggtggtggcg    300
aaaaaagggg ttgccgacct cgataaccgt gctctctcgg aagcgttgga aaaattatgg    360
cgccgccact gtcgcctggc tcgcgggtcc tgatagccct tattcgggtc tatcaacgcc    420
tgatcagtcc gctgcttggg ccgcattgtc gtttc                              455
```

<210> SEQ ID NO 4
<211> LENGTH: 528
<212> TYPE: DNA
<213> ORGANISM: Pseudomonas aeruginosa

<400> SEQUENCE: 4

```
tctgtcgcgt cgtcgcgcca aaggccgtaa gcgtctgacc gtctgattta ccggtacgg    60 gtggtgagtc gggacttcga ccgggacaag cgtctactga cagcccggca attcagcgca   120
gtcttcgact ctccgaccgg caaggtcccc ggcaagcacg tcctgctgct ggcgcgcgag   180
aacggtctcg atcaccccg cctgggcctg gtgatcggca agaagaacgt caagctcgcc    240
gtccagcgca atcgcctcaa acgcctgatc cgcgaatcgt tccgccataa ccaggaaacc    300
ctggctggct gggatatcgt ggtgatcgcg cgcaaaggcc tgggcgaact ggaaaatccg    360
gagctgcacc agcagttcgg caagctctgg aaacgcctgt tgcgcaatcg acctcgcacg    420
gaaagccctg ctgacgcccc tggcgtggcc gacggtactc atgcataggt cgatgcccgc    480
gcatcccgat ccctgtagtg tcatcccccc ttcgatgacc cggcaccg                 528
```

<210> SEQ ID NO 5
<211> LENGTH: 510
<212> TYPE: DNA
<213> ORGANISM: Corynebacterium diphtheriae

<400> SEQUENCE: 5

```
ccggtcgcgc aatcgtggct gcacgtcgta acaagggtcg taagagcctg accgcttaag     60
gtcactctta caagctcgaa tagaacgacg gtgctacctt cacagcacaa gctcagcaat    120
tccgaacagt tccgcgcaac gattcggaag ggcaagcgtg ctgggaggag caccgtcgtt    180
cttcattttt atgctgaggc gaccgcgggc aaccttgcaa ccgcaggcgg cccgcgattc    240
ggcctcgttg tgtccaaggc tgttggaaat gctgtgactc gtcaccgtgt ttcgcggcag    300
ttaaggcacg tagtaatcgc tatgaaagac cagttcccag cgtcatccca tgttgttgtg    360
agggcgatac cgccagcggc gacagcaagt tatgaggagt tgcgggcaga tgtgcaggca    420
```

```
gcactcgaca agctcaaccg caagcgataa ggcggttact cgccctcgtg ggctggttag    480
tcgcgcattg tttgatgcgg tgcggttcta                                     510

<210> SEQ ID NO 6
<211> LENGTH: 504
<212> TYPE: DNA
<213> ORGANISM: Chlamydia trachomatis

<400> SEQUENCE: 6
gctacaaaaa gtggaagaaa tcttttaaat cgtcgtcgcc gtcacggcag acattcctta    60
attgatctct aagatctttc atttgtgcat cggttaactc tacctaaaag tgcccgccta    120
ttgaaacgta aacaatttgt ttacgtgcag cgttgtgggc aatattgtcg tactgatcag    180
gcaactttac gaatagttcc ttctcgtcat tcgaacatcc gtaaagtagg ggttactgtt    240
tctaaaaaat ttgggaaagc ccatcagcgc aatcgcttta aagaattgt gcgagaggct     300 tttaggcatg tgcgaccaaa tcttcccgca tgtcaagtgg tagtgtctcc taagggggc     360 actctaccaa attttggtaa actatccgcg gatcttctta agcatattcc agaggctttg    420
cctctcgtta cttcttctaa gtagttttt attttggtca aaaataaaa aaccattcca      480 cgctatagag gcatggaatg ggaa                                           504

<210> SEQ ID NO 7
<211> LENGTH: 492
<212> TYPE: DNA
<213> ORGANISM: Vibrio cholerae

<400> SEQUENCE: 7
ggcagcgtgg gccgataagt ggactaataa accactggta aagttttaca ataccaatgg    60
ctaaccacga gaagggcgag agaggcgttg ccatagtttg ccaagcaagt taaacagttc    120
ttcattgctc aaatcttgcg cgctcttttt ggcgatgaca acaaaatctt tgttagccag    180
ttgattttga tgtaagcgaa agctttctct gcaaatacgt ttgaatcgat tacggccgac    240
ggcagttttg atctgctttt taggaaccgc gagtcccaaa cgaggatgag aaaggttatt    300
agcgcgagcg atgattgtga gatgaggaga accagcactg tgagcttgct ggaagacttt    360
ttgataatgt tcgggagtta acaaacgtaa ctcccgattg aatgcgtacg tactcaaaat    420
aattcgagat tattttgaca ggcgcttacg gccttttgca cgacgtgcat tcagaacttt    480
acgaccgttc gc                                                        492

<210> SEQ ID NO 8
<211> LENGTH: 492
<212> TYPE: DNA
<213> ORGANISM: Neisseria gonorrhoea

<400> SEQUENCE: 8
atgttccttg tatgggaaac ccgttgccgt ctgaaccttg cctgcagggt accgttctga    60
tcatacctgt ttcccgcatc cggttgcggg gttgccgaac atgagttgtg ccagttccgc    120
ccttgcctgt tttgcggtag ccctgtcgaa tttccggcgg acgcgcacga cgaaatcctg    180
aggcggcagc cggttttgt tcaatctgaa ccagtcgcgg atgacgcgtt tcatatagtt     240
ccgctcgttg gcgcgtttgg cggttttttt gccgaccacc agaccgatgc ggggatggtc    300
cagcccgttg ccgtttgagc gcgaaacttg cagcaggtcg cggctgcggc ggtttctgaa    360
tgcaaaaacg gatgaaaaat catccgtttt taacaagcgg tactgccttc cgaagcggta    420
gtccaaaatt acactgccag cgtttgcgg cctttggcac ggcgtgcggc caatactgcg     480
```

-continued cgtccgccgc gt                                                         492

<210> SEQ ID NO 9
<211> LENGTH: 492
<212> TYPE: DNA
<213> ORGANISM: Neisseria meningitidis

<400> SEQUENCE: 9
tgttccttag tatgggaaac ccgttgccgt ctgaaccttg cctgcagagt accgttctga     60
tcatgcctgt ttcctgcatc cggttgcggg gttgccgaac atgagttgtg ccagttccgc    120
ccttgcctgt tttgcggtag ccctgtcgaa tttacggcgg acgcgcacga cgaaatcctg    180
cggcggcagc cggttttttgt tcaatctgaa ccagtcgcgg atgacgcgct tcatataatt    240
tcgttcgttg gcgcgtttgg cggttttttt gccgaccacc agaccgatgc ggggatgatc    300
cagcccgttg ccgtttgaac gcgaaacttg cagcaggtcg cggctgcggc ggtttctgaa    360
tgcaaaaacg gatgaaaaat catccgtttt caacaagcgg tactgccttc cgaagcggta    420
gtccaaaatt acaccgccag gcgtttgcgg cctttggcgc ccgtgcggc caatactgcg    480 cgtccgccgc gc                                                         492

<210> SEQ ID NO 10
<211> LENGTH: 462
<212> TYPE: DNA
<213> ORGANISM: Streptococcus pyogenes

<400> SEQUENCE: 10
gttacctcac cacgaccaca ggccactaat aatagaacta agggactat tcttgcaatt     60 ttaatgtttt tcttcactct caaaaccttt ctcaagcaat gtgctaaact ttaaaacatg    120
atgtaaattt tgttgaagct cttgatactc caaagattcg acaccttac gggcaatcac    180 cacgaaatcc tctgacttca gctgatgccc taatgccatg ataacatgac gtatctttcg    240
tttgactgca tttctggtga ctgcattcc tattttttta ccgacagaaa tacccacacg    300
gaagtggtct tggcctctat ttaaatgata atgacaaat tttcgatttg ctgtactttt    360
tccatcctta aatatggctt ggaaatcttt ctcacgcttg acacgatagg tcttcttcaa    420
aatttaactc caatatctaa attattacca ttataccaca tc                       462

<210> SEQ ID NO 11
<211> LENGTH: 492
<212> TYPE: DNA
<213> ORGANISM: Bordetella pertussis

<400> SEQUENCE: 11
ccacccaggg gctgaggaag taccggtaaa accggatcgg ggcgataagc agtctcctga     60
tcatcgcgct atccgtgtga agtgagcatc tacttcggcg cgcgccgagc gtttcagggc    120
cgtgaggctt gccggtgtca gcttgctgtg cagccgcacc acgtaatcct gggccggcag    180
ggcaagccgg cgagcccgga acgcttcgcg gatgacccgc ttcaaggtat tgcgcgtcac    240
ggcgcgggcg gcaaaacgct tggcgatcac caggcccagg cgcgcgcgcg ccggctggtc    300
atcagcaggg gcacagggcg aggcgctgac aataaagaaa gccctcgggg ccagtcgccg    360
gcctttgagg gcggcggcaa actcggaggg gcgatgcaat cgcgcctccg cagggagcgt    420
ggcgcgcggc atgggtgacg tgacggagac tggcgacggg gccggcggcg atgctcctgt    480
tacaggcaat cc                                                         492

<210> SEQ ID NO 12
<211> LENGTH: 534
<212> TYPE: DNA
<213> ORGANISM: Porphyromonas gingivalis

<400> SEQUENCE: 12

```
agaagaaaat ggggagcagt aagagttgca cgagaaaagc cttgatcagt cgcatcgtat      60
ttactcgttt ttcaaagccg atgaaggtac atttccggca attctgatca gactcttttg     120
catcgctctc tccactgtac gaaagtcagg aagttcatcc gatactacca taatgcaat     180
agtagcatag atctgtctct cttggaggac atcgttcagg aggtgtttgt tgagccgata     240
agcctccctg accaaacgct tgaccctatt gcgcttcacg gctcgcctaa accttttctt     300
tgctacgctt accagcatgg aggaatatgc aactcgatgc tccgatccca gacggtagac     360
tacgcgtaga ggataaacga caaacgcctt gccttcgcca agaccgtat tgatttcatc      420
gcgaagatag aggcgttcgc ttttggatag gccgaatgta ggcggagagg tcatttcccg     480
ttgaggtaat cctctaatgc catagccata gaaggatatt gctcggtcgg cgca           534
```

<210> SEQ ID NO 13
<211> LENGTH: 495
<212> TYPE: DNA
<213> ORGANISM: Streptococcus pneumoniae

<400> SEQUENCE: 13

```
tcgctagtta ccccattagt cgcacaggct gtcatgatta acagagacag tcctagcaaa      60
ctagtcaact ttagtttctt tttcactccc atttccttcc cggtaaatct tgataatttt     120
taatacatgg agtagatttt tctccatctc tgcgtatccc aagtttcga ctccttttcg      180
agcaatgaca acaaagtcga catcttctac cagactccct tttgcattct ggataatatg     240
ccgaatccgt cgcttaattt gatttctagt gacggcattc cccagttttt tgctaactga     300
tagacctact cgaaaacggt ttttctggtt ttctaattgg tagaccacaa atttgcgatt     360
agcaaaactt gtcccctcct tgaaaatcgc cttaaaatct ttctctcttt ttacacgaaa     420
gtttttcttc aaaactcaac tccatctatt aaattactac tattatacca tattttttcaa    480
aaaagccaat catag                                                      495
```

<210> SEQ ID NO 14
<211> LENGTH: 465
<212> TYPE: DNA
<213> ORGANISM: Clostridium difficile

<400> SEQUENCE: 14

```
tcctttaata tataaattat tttattcaaa gtcattaacc tccatattta tagcatacaa      60
ttaaatagaa atatccgttc ttttaactaa attttttata gacttgtcta tgtctttaaa     120
agtagcatcc ttactagata cccttgctat aaatactata tcatatccag cttaattttt     180
ttcatcaata tttaatctgt aggcttcttt tattaatctt cttactctat tcctagtaat     240
agcttttcct acttttttttg aaacagaaat acctactcta ctataatctg atttattttt    300
aagtatatat attactaaat atttgtttgc aaaagatttg ccgtgtttat atacttttct     360
aaaatcagag tctttttttca acccttttagt cctattaaag tccatagtta acctccataa   420
acacagctat gaatcgtaat tatttacaca aaaaggccac ctttg                     465
```

<210> SEQ ID NO 15
<211> LENGTH: 447

-continued

<212> TYPE: DNA
<213> ORGANISM: Camphylobacter jejuni

<400> SEQUENCE: 15
aagcagcggg ttttaaaggg cttaagaatt tctgataaaa acggagtatt tttaggcata 60
tcatttgaaa cattctagtt ttttcaatcc ccattttaga tttttttcta acctagaaaa 120
agaaagttca gtgatttcat ttttagctac aaaaatatat ttgccatctt gaagatatct 180
ttcaaactta gcaaacaaag ctcttaaaat tcgttttgaa cgatttctaa ccactgcttt 240
tccaactttt ttactagcaa caactgctat ttttttttca taactattca gataaaaaat 300
gatcacacct tcgcaatgcc attttttgcc tactttatat acagatgaaa attcctcgtt 360
tgtgctaaat ttatcaaaat ttttcacaca gcaagtcttt ttctaccttt agcgcgtctt 420
gcattgatca ctttgcgacc attttta 447

<210> SEQ ID NO 16
<211> LENGTH: 480
<212> TYPE: DNA
<213> ORGANISM: Baccillus anthracis

<400> SEQUENCE: 16
taaacctaat ttctttttca aagcctactc ctccttgtat cggtatgtat atagtgtaat 60
tcatttcctt acgctacttt ttattctttt cataccagag cgtttaaaga catgaattaa 120
gcttttcttt aattcttcat atgtcatctc tgcacaaggc ttccttgcta ttataacaaa 180
atcttttcca gaatctatct catcttttaa ttctgtgatc gactggcgaa tcatacgttt 240
aattcggtta cgcactactg catttcctat cttcttgctg acagaaaggc caatacgaaa 300
gtttggctgc tcttctttat ctagttgata gacaacaaat tgacgattcg cattcgattt 360
tcctttttga aaaaccgtct ggaattcatc attctttttt atacgatgtt ttttcttcat 420
atcaattgac actcctgtag ttcatcagcg gaaattcact attattagaa aaaaagacca 480

<210> SEQ ID NO 17
<211> LENGTH: 480
<212> TYPE: DNA
<213> ORGANISM: Mycobacterium avium

<400> SEQUENCE: 17
gtccgcgggc gacggttcgg ccggcgccgc gaatggccgc gcccgaccgc gccggtccgg 60
tcacggcccg gttcccgccg gcatgcgccg caggcaccgc tgcagttcct gcgccaggcg 120
cgccgacgac gcggtccggc ttccgggcag cgcgcgaatc accagccggt cggatggttc 180
gagttcgccg agcagggccc gggccacgtg acgcagccgg cgggccacgc ggtgtcgttg 240
caccgccgtc ccgacggcct tcccgacgac cagcccgacc cgtgggcccg cggattcgtc 300
gtcgggttcg gagtcgcgcc ggaggtggac gacgatgtcg ggctgcgcca tgcgggttcc 360
gtgcttcacc gtcgcgtcaa actcggttga ccgcgtcatg cggttgcgtg cgggaagcac 420
cgcgaaagac ctgacgtgcg atcaggcaga gagcgcgcgg cgacccttgc ggcgccgacc 480

<210> SEQ ID NO 18
<211> LENGTH: 474
<212> TYPE: DNA
<213> ORGANISM: Staphylococcus aureus

<400> SEQUENCE: 18
gttataagct caatagaagt ttaaatatag cttcaaataa aaacgataaa taagcgagtg 60

```
atgttattgg aaaaagctta ccgaattaaa aagaatgcag attttcagag aatatataaa    120
aaaggtcatt ctgtagccaa cagacaattt gttgtataca cttgtaataa taaagaaata    180
gaccattttc gcttaggtat tagtgtttct aaaaaactag gtaatgcagt gttaagaaac    240
aagattaaaa gagcaatacg tgaaaatttc aaagtacata agtcgcatat attggccaaa    300
gatattattg taatagcaag acagccagct aaagatatga cgactttaca aatacagaat    360
agtcttgagc acgtacttaa aattgccaaa gttttaata aaaagattaa gtaaggatag     420
ggtaggggaa ggaaaacatt aaccactcaa cacatcccga agtcttacct caga           474
```

<210> SEQ ID NO 19
<211> LENGTH: 474
<212> TYPE: DNA
<213> ORGANISM: Staphylococcus aureus

<400> SEQUENCE: 19

```
gttataagct caatagaagt ttaaatatag cttcaaataa aaacgataaa taagcgagtg     60
atgttattgg aaaaagctta ccgaattaaa aagaatgcag attttcagag aatatataaa    120
aaaggtcatt ctgtagccaa cagacaattt gttgtataca cttgtaataa taaagaaata    180
gaccattttc gcttaggtat tagtgtttct aaaaaactag gtaatgcagt gttaagaaac    240
aagattaaaa gagcaatacg tgaaaatttc aaagtacata agtcgcatat attggccaaa    300
gatattattg taatagcaag acagccagct aaagatatga cgactttaca aatacagaat    360
agtcttgagc acgtacttaa aattgccaaa gttttaata aaaagattaa gtaaggatag     420
ggtaggggaa ggaaaacatt aaccactcaa cacatcccga agtcttacct caga           474
```

<210> SEQ ID NO 20
<211> LENGTH: 119
<212> TYPE: PRT
<213> ORGANISM: Streptococcus mutans

<400> SEQUENCE: 20

```
Val Leu Lys Lys Ala Tyr Arg Val Lys Ser Asp Lys Asp Phe Gln Ala
  1               5                  10                  15

Ile Phe Thr Glu Gly Arg Ser Val Ala Asn Arg Lys Phe Val Val Tyr
                 20                  25                  30

Ser Leu Glu Lys Asp Gln Ser His Tyr Arg Val Gly Leu Ser Val Gly
             35                  40                  45

Lys Arg Leu Gly Asn Ala Val Val Arg Asn Ala Ile Lys Arg Lys Leu
         50                  55                  60

Arg His Val Leu Met Glu Leu Gly Pro Tyr Leu Gly Thr Gln Asp Phe
 65                  70                  75                  80

Val Val Ile Ala Arg Lys Gly Val Glu Glu Leu Asp Tyr Ser Thr Met
                 85                  90                  95

Lys Lys Asn Leu Val His Val Lys Leu Ala Lys Leu Tyr Gln Glu
                100                 105                 110

Gly Ser Ile Arg Glu Lys Glu
        115
```

<210> SEQ ID NO 21
<211> LENGTH: 119
<212> TYPE: PRT
<213> ORGANISM: Klebsiella pneumoniae

<400> SEQUENCE: 21

Val Val Lys Leu Ala Phe Pro Arg Glu Leu Arg Leu Leu Thr Pro Ser

```
             1               5                   10                  15
His Phe Thr Phe Val Phe Gln Gln Pro Gln Arg Ala Gly Thr Pro Gln
                    20                  25                  30

Ile Thr Ile Leu Gly Arg Leu Asn Ser Leu Gly His Pro Arg Ile Gly
            35                  40                  45

Leu Thr Val Ala Lys Lys Asn Val Lys Arg Ala His Glu Arg Asn Arg
        50                  55                  60

Ile Lys Arg Leu Thr Arg Glu Ser Phe Arg Leu Arg Gln His Glu Leu
 65                 70                  75                  80

Pro Pro Met Asp Phe Val Val Ala Lys Arg Gly Val Ala Asp Leu
                85                  90                  95

Asp Asn Arg Ala Leu Ser Glu Ala Leu Glu Lys Leu Trp Arg Arg His
            100                 105                 110

Cys Arg Leu Ala Arg Gly Ser
            115

<210> SEQ ID NO 22
<211> LENGTH: 110
<212> TYPE: PRT
<213> ORGANISM: Salmonella paratyphi

<400> SEQUENCE: 22

Val Thr Phe Val Asn Ser Arg Ser Phe His Ile Arg Leu Pro Ala Thr
 1               5                   10                  15

Ser Thr Gly Cys Thr Pro Gln Ile Thr Ile Leu Gly Arg Leu Asn Ser
                20                  25                  30

Leu Gly His Pro Arg Ile Gly Leu Thr Val Ala Lys Lys Asn Val Arg
            35                  40                  45

Arg Ala His Glu Arg Asn Arg Ile Lys Arg Leu Thr Arg Glu Ser Phe
        50                  55                  60

Arg Leu Arg Gln His Glu Leu Pro Ala Met Asp Phe Val Val Ala
 65                 70                  75                  80

Lys Lys Gly Val Ala Asp Leu Asp Asn Arg Ala Leu Ser Glu Ala Leu
                85                  90                  95

Glu Lys Leu Trp Arg Arg His Cys Arg Leu Ala Arg Gly Ser
            100                 105                 110

<210> SEQ ID NO 23
<211> LENGTH: 135
<212> TYPE: PRT
<213> ORGANISM: Pseudomonas aeruginosa

<400> SEQUENCE: 23

Val Val Ser Arg Asp Phe Asp Arg Asp Lys Arg Leu Leu Thr Ala Arg
 1               5                   10                  15

Gln Phe Ser Ala Val Phe Asp Ser Pro Thr Gly Lys Val Pro Gly Lys
                20                  25                  30

His Val Leu Leu Leu Ala Arg Glu Asn Gly Leu Asp His Pro Arg Leu
            35                  40                  45

Gly Leu Val Ile Gly Lys Lys Asn Val Lys Leu Ala Val Gln Arg Asn
        50                  55                  60

Arg Leu Lys Arg Leu Ile Arg Glu Ser Phe Arg His Asn Gln Glu Thr
 65                 70                  75                  80

Leu Ala Gly Trp Asp Ile Val Val Ile Ala Arg Lys Gly Leu Gly Glu
                85                  90                  95

Leu Glu Asn Pro Glu Leu His Gln Gln Phe Gly Lys Leu Trp Lys Arg
```

-continued

```
            100                 105                 110

Leu Leu Arg Asn Arg Pro Arg Thr Glu Ser Pro Ala Asp Ala Pro Gly
        115                 120                 125
Val Ala Asp Gly Thr His Ala
    130                 135

<210> SEQ ID NO 24
<211> LENGTH: 129
<212> TYPE: PRT
<213> ORGANISM: Corynebacterium diphtheriae

<400> SEQUENCE: 24

Val Thr Leu Thr Ser Ser Asn Arg Thr Thr Val Leu Pro Ser Gln His
 1               5                  10                  15
Lys Leu Ser Asn Ser Glu Gln Phe Arg Ala Thr Ile Arg Lys Gly Lys
            20                  25                  30
Arg Ala Gly Arg Ser Thr Val Val Leu His Phe Tyr Ala Glu Ala Thr
        35                  40                  45

Ala Gly Asn Leu Ala Thr Ala Gly Gly Pro Arg Phe Gly Leu Val Val
    50                  55                  60

Ser Lys Ala Val Gly Asn Ala Val Thr Arg His Arg Val Ser Arg Gln
65                  70                  75                  80

Leu Arg His Val Val Ile Ala Met Lys Asp Gln Phe Pro Ala Ser Ser
                85                  90                  95

His Val Val Val Arg Ala Ile Pro Pro Ala Ala Thr Ala Ser Tyr Glu
            100                 105                 110

Glu Leu Arg Ala Asp Val Gln Ala Ala Leu Asp Lys Leu Asn Arg Lys
        115                 120                 125

Arg

<210> SEQ ID NO 25
<211> LENGTH: 119
<212> TYPE: PRT
<213> ORGANISM: Chlamydia trachomatis

<400> SEQUENCE: 25

Val His Arg Leu Thr Leu Pro Lys Ser Ala Arg Leu Leu Lys Arg Lys
 1               5                  10                  15

Gln Phe Val Tyr Val Gln Arg Cys Gly Gln Tyr Cys Arg Thr Asp Gln
            20                  25                  30

Ala Thr Leu Arg Ile Val Pro Ser Arg His Ser Asn Ile Arg Lys Val
        35                  40                  45

Gly Val Thr Val Ser Lys Lys Phe Gly Lys Ala His Gln Arg Asn Arg
    50                  55                  60

Phe Lys Arg Ile Val Arg Glu Ala Phe Arg His Val Arg Pro Asn Leu
65                  70                  75                  80

Pro Ala Cys Gln Val Val Val Ser Pro Lys Gly Gly Thr Leu Pro Asn
                85                  90                  95

Phe Gly Lys Leu Ser Ala Asp Leu Leu Lys His Ile Pro Glu Ala Leu
            100                 105                 110

Pro Leu Val Thr Ser Ser Lys
        115

<210> SEQ ID NO 26
<211> LENGTH: 122
<212> TYPE: PRT
<213> ORGANISM: Vibrio cholerae
```

<400> SEQUENCE: 26

Ser Arg Ile Ile Leu Ser Thr Tyr Ala Phe Asn Arg Glu Leu Arg Leu
1               5                   10                  15

Leu Thr Pro Glu His Tyr Gln Lys Val Phe Gln Ala His Ser Ala
            20                  25                  30

Gly Ser Pro His Leu Thr Ile Ile Ala Arg Ala Asn Asn Leu Ser His
            35                  40                  45

Pro Arg Leu Gly Leu Ala Val Pro Lys Lys Gln Ile Lys Thr Ala Val
50                  55                  60

Gly Arg Asn Arg Phe Lys Arg Ile Cys Arg Glu Ser Phe Arg Leu His
65                  70                  75                  80

Gln Asn Gln Leu Ala Asn Lys Asp Phe Val Val Ile Ala Lys Lys Ser
                85                  90                  95

Ala Gln Asp Leu Ser Asn Glu Glu Leu Phe Asn Leu Leu Gly Lys Leu
            100                 105                 110

Trp Gln Arg Leu Ser Arg Pro Ser Arg Gly
            115                 120

<210> SEQ ID NO 27
<211> LENGTH: 123
<212> TYPE: PRT
<213> ORGANISM: Neisseria gonorrhoea

<400> SEQUENCE: 27

Val Ile Leu Asp Tyr Arg Phe Gly Arg Gln Tyr Arg Leu Leu Lys Thr
1               5                   10                  15

Asp Asp Phe Ser Ser Val Phe Ala Phe Arg Asn Arg Arg Ser Arg Asp
            20                  25                  30

Leu Leu Gln Val Ser Arg Ser Asn Gly Asn Gly Leu Asp His Pro Arg
            35                  40                  45

Ile Gly Leu Val Val Gly Lys Lys Thr Ala Lys Arg Ala Asn Glu Arg
50                  55                  60

Asn Tyr Met Lys Arg Val Ile Arg Asp Trp Phe Arg Leu Asn Lys Asn
65                  70                  75                  80

Arg Leu Pro Pro Gln Asp Phe Val Val Arg Val Arg Arg Lys Phe Asp
                85                  90                  95

Arg Ala Thr Ala Lys Gln Ala Arg Ala Glu Leu Ala Gln Leu Met Phe
            100                 105                 110

Gly Asn Pro Ala Thr Gly Cys Gly Lys Gln Val
            115                 120

<210> SEQ ID NO 28
<211> LENGTH: 123
<212> TYPE: PRT
<213> ORGANISM: Neisseria meningitidis

<400> SEQUENCE: 28

Val Ile Leu Asp Tyr Arg Phe Gly Arg Gln Tyr Arg Leu Leu Lys Thr
1               5                   10                  15

Asp Asp Phe Ser Ser Val Phe Ala Phe Arg Asn Arg Arg Ser Arg Asp
            20                  25                  30

Leu Leu Gln Val Ser Arg Ser Asn Gly Asn Gly Leu Asp His Pro Arg
            35                  40                  45

Ile Gly Leu Val Val Gly Lys Lys Thr Ala Lys Arg Ala Asn Glu Arg
50                  55                  60

-continued

```
Asn Tyr Met Lys Arg Val Ile Arg Asp Trp Phe Arg Leu Asn Lys Asn
65                  70                  75                  80

Arg Leu Pro Pro Gln Asp Phe Val Val Arg Val Arg Arg Lys Phe Asp
                85                  90                  95

Arg Ala Thr Ala Lys Gln Ala Arg Ala Glu Leu Ala Gln Leu Met Phe
            100                 105                 110

Gly Asn Pro Ala Thr Gly Cys Arg Lys Gln Ala
        115                 120

<210> SEQ ID NO 29
<211> LENGTH: 113
<212> TYPE: PRT
<213> ORGANISM: Streptococcus pyogenes

<400> SEQUENCE: 29

Val Lys Arg Glu Lys Asp Phe Gln Ala Ile Phe Lys Asp Gly Lys Ser
 1               5                  10                  15

Thr Ala Asn Arg Lys Phe Val Ile Tyr His Leu Asn Arg Gly Gln Asp
            20                  25                  30

His Phe Arg Val Gly Ile Ser Val Gly Lys Lys Ile Gly Asn Ala Val
        35                  40                  45

Thr Arg Asn Ala Val Lys Arg Lys Ile Arg His Val Ile Met Ala Leu
    50                  55                  60

Gly His Gln Leu Lys Ser Glu Asp Phe Val Val Ile Ala Arg Lys Gly
65                  70                  75                  80

Val Glu Ser Leu Glu Tyr Gln Glu Leu Gln Gln Asn Leu His His Val
                85                  90                  95

Leu Lys Leu Ala Gln Leu Leu Glu Lys Gly Phe Glu Ser Glu Glu Lys
            100                 105                 110

His

<210> SEQ ID NO 30
<211> LENGTH: 123
<212> TYPE: PRT
<213> ORGANISM: Bordetella pertussis

<400> SEQUENCE: 30

Met Pro Arg Ala Thr Leu Pro Ala Glu Ala Arg Leu His Arg Pro Ser
 1               5                  10                  15

Glu Phe Ala Ala Ala Leu Lys Gly Arg Arg Leu Ala Arg Gly Ala Phe
            20                  25                  30

Phe Ile Val Ser Ala Ser Pro Cys Ala Pro Ala Asp Asp Gln Pro Ala
        35                  40                  45

Arg Ala Arg Leu Gly Leu Val Ile Ala Lys Arg Phe Ala Ala Arg Ala
    50                  55                  60

Val Thr Arg Asn Thr Leu Lys Arg Val Ile Arg Glu Ala Phe Arg Ala
65                  70                  75                  80

Arg Arg Leu Ala Leu Pro Ala Gln Asp Tyr Val Val Arg Leu His Ser
                85                  90                  95

Lys Leu Thr Pro Ala Ser Leu Thr Ala Leu Lys Arg Ser Ala Arg Ala
            100                 105                 110

Glu Val Asp Ala His Phe Thr Arg Ile Ala Arg
        115                 120

<210> SEQ ID NO 31
<211> LENGTH: 137
<212> TYPE: PRT
```

```
<213> ORGANISM: Porphyromonas gingivalis

<400> SEQUENCE: 31

Met Thr Ser Pro Pro Thr Phe Gly Leu Ser Lys Ser Glu Arg Leu Tyr
1               5                   10                  15

Leu Arg Asp Glu Ile Asn Thr Val Phe Gly Glu Gly Lys Ala Phe Val
            20                  25                  30

Val Tyr Pro Leu Arg Val Val Tyr Arg Leu Gly Ser Glu His Arg Val
        35                  40                  45

Ala Tyr Ser Ser Met Leu Val Ser Val Ala Lys Lys Arg Phe Arg Arg
    50                  55                  60

Ala Val Lys Arg Asn Arg Val Lys Arg Leu Val Arg Glu Ala Tyr Arg
65                  70                  75                  80

Leu Asn Lys His Leu Leu Asn Asp Val Leu Gln Glu Arg Gln Ile Tyr
                85                  90                  95

Ala Thr Ile Ala Phe Met Val Val Ser Asp Glu Leu Pro Asp Phe Arg
            100                 105                 110

Thr Val Glu Arg Ala Met Gln Lys Ser Leu Ile Arg Ile Ala Gly Asn
        115                 120                 125

Val Pro Ser Ser Ala Leu Lys Asn Glu
    130                 135

<210> SEQ ID NO 32
<211> LENGTH: 124
<212> TYPE: PRT
<213> ORGANISM: Streptococcus pneumoniae

<400> SEQUENCE: 32

Val Leu Lys Lys Asn Phe Arg Val Lys Arg Glu Lys Asp Phe Lys Ala
1               5                   10                  15

Ile Phe Lys Glu Gly Thr Ser Phe Ala Asn Arg Lys Phe Val Val Tyr
            20                  25                  30

Gln Leu Glu Asn Gln Lys Asn Arg Phe Arg Val Gly Leu Ser Val Ser
        35                  40                  45

Lys Lys Leu Gly Asn Ala Val Thr Arg Asn Gln Ile Lys Arg Arg Ile
    50                  55                  60

Arg His Ile Ile Gln Asn Ala Lys Gly Ser Leu Val Glu Asp Val Asp
65                  70                  75                  80

Phe Val Val Ile Ala Arg Lys Gly Val Glu Thr Leu Gly Tyr Ala Glu
            85                  90                  95

Met Glu Lys Asn Leu Leu His Val Leu Lys Leu Ser Lys Ile Tyr Arg
            100                 105                 110

Glu Gly Asn Gly Ser Glu Lys Glu Thr Lys Val Asp
        115                 120

<210> SEQ ID NO 33
<211> LENGTH: 114
<212> TYPE: PRT
<213> ORGANISM: Clostridium difficile

<400> SEQUENCE: 33

Met Asp Phe Asn Arg Thr Lys Gly Leu Lys Lys Asp Ser Asp Phe Arg
1               5                   10                  15

Lys Val Tyr Lys His Gly Lys Ser Phe Ala Asn Lys Tyr Leu Val Ile
            20                  25                  30

Tyr Ile Leu Lys Asn Lys Ser Asp Tyr Ser Arg Val Gly Ile Ser Val
        35                  40                  45
```

-continued

```
Ser Lys Lys Val Gly Lys Ala Ile Thr Arg Asn Arg Val Arg Arg Leu
    50                  55                  60

Ile Lys Glu Ala Tyr Arg Leu Asn Ile Asp Glu Lys Ile Lys Pro Gly
65                  70                  75                  80

Tyr Asp Ile Val Phe Ile Ala Arg Val Ser Ser Lys Asp Ala Thr Phe
                85                  90                  95

Lys Asp Ile Asp Lys Ser Ile Lys Asn Leu Val Lys Arg Thr Asp Ile
            100                 105                 110

Ser Ile

<210> SEQ ID NO 34
<211> LENGTH: 108
<212> TYPE: PRT
<213> ORGANISM: Camphylobacter jejuni

<400> SEQUENCE: 34

Val Lys Asn Phe Asp Lys Phe Ser Thr Asn Glu Glu Phe Ser Ser Val
 1               5                  10                  15

Tyr Lys Val Gly Lys Lys Trp His Cys Glu Gly Val Ile Ile Phe Tyr
            20                  25                  30

Leu Asn Ser Tyr Glu Lys Lys Ile Ala Val Val Ala Ser Lys Lys Val
        35                  40                  45

Gly Lys Ala Val Val Arg Asn Arg Ser Lys Arg Ile Leu Arg Ala Leu
    50                  55                  60

Phe Ala Lys Phe Glu Arg Tyr Leu Gln Asp Gly Lys Tyr Ile Phe Val
65                  70                  75                  80

Ala Lys Asn Glu Ile Thr Glu Leu Ser Phe Ser Arg Leu Glu Lys Asn
                85                  90                  95

Leu Lys Trp Gly Leu Lys Lys Leu Glu Cys Phe Lys
            100                 105

<210> SEQ ID NO 35
<211> LENGTH: 119
<212> TYPE: PRT
<213> ORGANISM: Bacillus anthracis

<400> SEQUENCE: 35

Met Lys Lys Lys His Arg Ile Lys Lys Asn Asp Glu Phe Gln Thr Val
 1               5                  10                  15

Phe Gln Lys Gly Lys Ser Asn Ala Asn Arg Gln Phe Val Val Tyr Gln
            20                  25                  30

Leu Asp Lys Glu Glu Gln Pro Asn Phe Arg Ile Gly Leu Ser Val Ser
        35                  40                  45

Lys Lys Ile Gly Asn Ala Val Val Arg Asn Arg Ile Lys Arg Met Ile
    50                  55                  60

Arg Gln Ser Ile Thr Glu Leu Lys Asp Glu Ile Asp Ser Gly Lys Asp
65                  70                  75                  80

Phe Val Ile Ile Ala Arg Lys Pro Cys Ala Glu Met Thr Tyr Glu Glu
                85                  90                  95

Leu Lys Lys Ser Leu Ile His Val Phe Lys Arg Ser Gly Met Lys Arg
            100                 105                 110

Ile Lys Ser Ser Val Arg Lys
        115

<210> SEQ ID NO 36
<211> LENGTH: 119
```

```
<212> TYPE: PRT
<213> ORGANISM: Mycobacterium avium

<400> SEQUENCE: 36

Val Leu Pro Ala Arg Asn Arg Met Thr Arg Ser Thr Glu Phe Asp Ala
1               5                   10                  15

Thr Val Lys His Gly Thr Arg Met Ala Gln Pro Asp Ile Val Val His
            20                  25                  30

Leu Arg Arg Asp Ser Glu Pro Asp Glu Ser Ala Gly Pro Arg Val
        35                  40                  45

Gly Leu Val Val Gly Lys Ala Val Gly Thr Ala Val Gln Arg His Arg
    50                  55                  60

Val Ala Arg Arg Leu Arg His Val Ala Arg Ala Leu Leu Gly Glu Leu
65                  70                  75                  80

Glu Pro Ser Asp Arg Leu Val Ile Arg Ala Leu Pro Gly Ser Arg Thr
                85                  90                  95

Ala Ser Ser Ala Arg Leu Ala Gln Glu Leu Gln Arg Cys Leu Arg Arg
            100                 105                 110

Met Pro Ala Gly Thr Gly Pro
        115

<210> SEQ ID NO 37
<211> LENGTH: 117
<212> TYPE: PRT
<213> ORGANISM: Staphylococcus aureus

<400> SEQUENCE: 37

Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80

Asp Ile Ile Val Ile Ala Arg Gln Pro Ala Lys Asp Met Thr Thr Leu
                85                  90                  95

Gln Ile Gln Asn Ser Leu Glu His Val Leu Lys Ile Ala Lys Val Phe
            100                 105                 110

Asn Lys Lys Ile Lys
        115

<210> SEQ ID NO 38
<211> LENGTH: 117
<212> TYPE: PRT
<213> ORGANISM: Staphylococcus aureus

<400> SEQUENCE: 38

Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
```

-continued

```
                 50                  55                  60
Ala Ile Arg Glu Asn Phe Lys Val His Lys Ser His Ile Leu Ala Lys
 65                  70                  75                  80

Asp Ile Ile Val Ile Ala Arg Gln Pro Ala Lys Asp Met Thr Thr Leu
                 85                  90                  95

Gln Ile Gln Asn Ser Leu Glu His Val Leu Lys Ile Ala Lys Val Phe
            100                 105                 110

Asn Lys Lys Ile Lys
        115

<210> SEQ ID NO 39
<211> LENGTH: 360
<212> TYPE: DNA
<213> ORGANISM: Pasteurella multocida

<400> SEQUENCE: 39
gtgattaagc tgaatttttc gagggagtta cgtttgttaa ctccccttca ttttaaatac      60
gtcttcgaac agccgttccg tgctagtaca cctgaactta ccattcttgc tcgtcccaat     120
aatctcgctc atcctcgctt agggttaact gtcgcgaaaa agcatttaaa aaaagcacat     180
gatcgcaatc gcatcaaacg cttatgccga aaagtttccg cctagcaca gtataaactc      240 cccaattgcg atttttgttat tgtggcgaaa cagggaattg gtaaattaga caacaggaca     300
ctcacacaaa cattggataa attatggcaa agacacattc gcttagctca aaatcttga      360

<210> SEQ ID NO 40
<211> LENGTH: 372
<212> TYPE: DNA
<213> ORGANISM: Haemophilus ducreyi

<400> SEQUENCE: 40 ttaattttg ctttgtgctt gttgactgag gcgaatatga cgagtccata atttatctat       60
ggttgcgaaa agcgtagcat tatctagttt accaatccca tgcttggcaa caaagacaaa     120
gtcaaaatta ggtaattgat gttgttttaa acggaagctt tcccgcacaa tacgtttgat     180
ccgattgcga tcgtgagcac gttttaaatg cttttttagca acggttaacc caagacgagg    240
cgtattaacg caattttgac gagcaagaat agtaagttca gctgtgctag cacgatatgg    300
ttgttcaaac acggctttga attgaatggg agctaacaaa cgtagctccc gagaaaacgt    360
tagcttattc ac                                                          372

<210> SEQ ID NO 41
<211> LENGTH: 360
<212> TYPE: DNA
<213> ORGANISM: Chlamydia muridarum

<400> SEQUENCE: 41
gtgcatcggt taactctacc taaaagtgcc cgcctattga aacgtaaaca atttgtttac      60
gtgcagcgtt gtgggcaata ttgtcgtact gatcaggcaa ctttacgaat agttccttct    120
cgtcattcga acatccgtaa agtaggggtt actgtttcta aaaaatttgg gaaagcccat    180
cagcgcaatc gctttaaaag aattgtgcga gaggctttta ggcatgtgcg accaaatctt    240
cccgcatgtc aagtggtagt gtctcctaaa gggggcactc taccaaattt tggtaaacta    300
tccgcggatc ttcttaagca tattccagag gctttgcctc tcgttacttc ttctaagtag     360

<210> SEQ ID NO 42
<211> LENGTH: 420
```

-continued

<212> TYPE: DNA
<213> ORGANISM: Chlamydophila psittaci

<400> SEQUENCE: 42

```
gtgcatcgat caaccttacc caaatatgct cgtgtgttaa agagaaagca gtttctctac      60
atctcgcgag cgggatctca ctgtcaaggc agtcaggtta ttttcatgt tgctccatct     120
agatattctg gatgttgcaa gcttgggata actgtctcaa aaaatttgg gaaagcgcat     180
aaagaaatt attttaaacg tattgtgcgc gaggcttttc gtaaaaagcg tcactctctt     240
cctgcttgtc aaattgttgt tatgcctaaa acaagcagc aacctaaatt tgaagatctg     300
cttcaagact ttgctcagca aattccagaa gcactcagta gcaaattagc aaaaaataag     360
cctacgactg gtgtcgaata tagtccaaag aatgagaaat gtgagtctgt acttccttag    420
```

<210> SEQ ID NO 43
<211> LENGTH: 357
<212> TYPE: DNA
<213> ORGANISM: Treponema denticola

<400> SEQUENCE: 43

```
tcataaagcc tcatcattat acattttcgc ttttaaaaag agggcggtaa gttgttctaa      60
acgaagagaa taagaatcct tttctgaaaa accagcagg ataatgtcgt ttcccgtttt     120
taacctatgt tttatatgtc tataggcctc ttttgatatt ctccgagacc tgttccgcat    180
cactgcggaa ccgaaacctc gtcgaaaagt acataagaat cgattgtact ccaatccatt    240
aggcaggatt aacaaactaa ctccgtttaa gctaagttta agaccttttt gaaatacggc    300
cttaatacat gaccgatccc ttaaccgttc ttcaccggaa aatgtaaaat tactcac      357
```

<210> SEQ ID NO 44
<211> LENGTH: 357
<212> TYPE: DNA
<213> ORGANISM: Enterococcus faecalis

<400> SEQUENCE: 44

```
ctactcaatt ccctctctta catctaatat tttagctaaa tttaacacat gtgttaaatt      60
agctttcact tcttcagacg ataactttc caatcctgga cgtgcaatca cgataaaatc    120
aatttctgga gagatacggt cttttaattg aaataaactc gcgcggattt tccgcttcac    180
agcatttctt gtgaccgcgt ttccaatttt cttcccaaca gaaatcccca ctcgaaaatg    240
ggcttgttgt ggtttctcta aaacgtacac cacgaaacga cgatttgcac aagattgttt    300
tttattaaac acctgttgaa attctttttc tttcttgaca cggtaggact ttttcat      357
```

<210> SEQ ID NO 45
<211> LENGTH: 330
<212> TYPE: DNA
<213> ORGANISM: Legionella pneumophila

<400> SEQUENCE: 45
ctatttgccg tagcatgagg ctaatttttc ccatgtttta tttaatttag tatttatacc 60
taaattggtt ttctttgcta gacctggtct tgccaaaatg attatatcta cagcaggcaa 120
gttagtatga cgaaaacttt ctctaagtag ccgtttaatg cgatttctgt catgagcctt 180
agctatcatt ttttttgaca atgctaaacc aaggcgtgca tagcctaact tattttctct 240
gaaaaggaaa ataaagtcat ctgtaggtat ttttttcgcg ctttgaaaca cgaagtcaaa 300
atgatttttt tttaataagc ggtgcggctg 330

-continued

<210> SEQ ID NO 46
<211> LENGTH: 348
<212> TYPE: DNA
<213> ORGANISM: Staphylococcus epidermis

<400> SEQUENCE: 46
ctacttaatc tttttattaa acacttttgc aattttaagc acatgctcta aactgctttg 60
aatctccagt gtattcatat cttttgctgg ttgcctcgca ataactataa tatctttagc 120
gataatattt tgcttatgca ctttaaaatt ctctcttatc gctcttttaa ttctatttct 180
tgtaacagcg ttgcccagtt tttttgagac acttattcct aagcgaaaat gttttaaatc 240
tctattttta taggtataga caacaaattg tctatttgca acagacttcc cattcttgta 300
tatcgcttga aagtctgaat ttctcttaat acgatatgct ttttccat 348

<210> SEQ ID NO 47
<211> LENGTH: 393
<212> TYPE: DNA
<213> ORGANISM: Mycobacterium smegmatis

<400> SEQUENCE: 47
tcatggggac gccctgcgct tcgagctcac ccgctcgagc gcttgaccca actgtcgttc 60
caaacgggac gacgtggcgt cacgactgct cggcctggcc cggatcacga tgagatcggc 120
agggtcaaga ccggatacga acgttttggc gacgtgccgc agacggcggg acacgcggtg 180
acgctccacc gcgttgccga cggctttgga cacgatcaga ccgatccgcg gcccgttcgc 240
gtcgccgtca tcgccgtcat cgccggcatt gcctgcgttg ctttcaaggc gcaacgcgtg 300
tacgacgaca tcgggttgcg cggcacgcac gccgcgactg acggtgacac tgaactccgc 360
ggaccgcctc atccggtttc gagccggaag cac 393

<210> SEQ ID NO 48
<211> LENGTH: 291
<212> TYPE: DNA
<213> ORGANISM: Burkholderia pseudomallei

<400> SEQUENCE: 48
cgcatgcagg cgcagcagaa tgtcccagcc ggcgaactcg gcgcgacgcg tacgaaacgc 60
ctcgcgggcg agccgcttga ccagattgcg cgtcaccgca cgcgcggcgt acttcttgcc 120
gatgacgagc ccaagacgcg catcgcgccc cgtcggcttg ccgtagatca cgaagtgcgc 180
ggtgcgccgc cagggacgca aacgaaaaac ggatgagaat tcatccgttt tcagaagtcg 240
cgcagctttg gggaaggcgg cggacgcttg caacggaatc gaaccccgga c 291

<210> SEQ ID NO 49
<211> LENGTH: 342
<212> TYPE: DNA
<213> ORGANISM: Ureaplasma urealyticum

<400> SEQUENCE: 49
ttatcttttt tctttgttaa taattcgttg aagaattatt ttaagattat tacaatttaa 60
aacaaaagaa ccatcaataa acgatggttt cactaagact acaatatcat aacttttaat 120
gggaatatca gcagcaataa accatgcttt aatcaggcgt cgaattcgat tgcgttgtgt 180
tgctaattta aacttttttt tagaaatgct tatagctaag cgaacatttt ttagattggt 240
tttacgaaaa taaactacga tttgattaga atgaattttt tgttgtttct taattgtatc 300
aagtatatct tcattttttt ttagactaat aaaattagcc at 342

-continued

<210> SEQ ID NO 50
<211> LENGTH: 119
<212> TYPE: PRT
<213> ORGANISM: Pasteurella multocida

<400> SEQUENCE: 50

```
Val Ile Lys Leu Asn Phe Ser Arg Glu Leu Arg Leu Leu Thr Pro Leu
 1              5                   10                  15

His Phe Lys Tyr Val Phe Glu Gln Pro Phe Arg Ala Ser Thr Pro Glu
            20                  25                  30

Leu Thr Ile Leu Ala Arg Pro Asn Asn Leu Ala His Pro Arg Leu Gly
        35                  40                  45

Leu Thr Val Ala Lys Lys His Leu Lys Lys Ala His Asp Arg Asn Arg
    50                  55                  60

Ile Lys Arg Leu Cys Arg Glu Ser Phe Arg Leu Ala Gln Tyr Lys Leu
65                  70                  75                  80

Pro Asn Cys Asp Phe Val Ile Val Ala Lys Gln Gly Ile Gly Lys Leu
                85                  90                  95

Asp Asn Arg Thr Leu Thr Gln Thr Leu Asp Lys Leu Trp Gln Arg His
            100                 105                 110

Ile Arg Leu Ala Gln Lys Ser
        115
```

<210> SEQ ID NO 51
<211> LENGTH: 123
<212> TYPE: PRT
<213> ORGANISM: Haemophilus ducreyi

<400> SEQUENCE: 51

```
Val Asn Lys Leu Thr Phe Ser Arg Glu Leu Arg Leu Leu Ala Pro Ile
 1              5                   10                  15

Gln Phe Lys Ala Val Phe Glu Gln Pro Tyr Arg Ala Ser Thr Ala Glu
            20                  25                  30

Leu Thr Ile Leu Ala Arg Gln Asn Cys Val Asn Thr Pro Arg Leu Gly
        35                  40                  45

Leu Thr Val Ala Lys Lys His Leu Lys Arg Ala His Asp Arg Asn Arg
    50                  55                  60

Ile Lys Arg Ile Val Arg Glu Ser Phe Arg Leu Lys Gln His Gln Leu
65                  70                  75                  80

Pro Asn Phe Asp Phe Val Phe Val Ala Lys His Gly Ile Gly Lys Leu
                85                  90                  95

Asp Asn Ala Thr Leu Phe Ala Thr Ile Asp Lys Leu Trp Thr Arg His
            100                 105                 110

Ile Arg Leu Ser Gln Gln Ala Gln Ser Lys Asn
        115                 120
```

<210> SEQ ID NO 52
<211> LENGTH: 119
<212> TYPE: PRT
<213> ORGANISM: Chlamydia muridarum

<400> SEQUENCE: 52

```
Met His Arg Leu Thr Leu Pro Lys Ser Ala Arg Leu Leu Lys Arg Lys
 1              5                   10                  15

Gln Phe Val Tyr Val Gln Arg Cys Gly Gln Tyr Cys Arg Thr Asp Gln
            20                  25                  30
```

-continued

```
Ala Thr Leu Arg Ile Val Pro Ser Arg His Ser Asn Ile Arg Lys Val
        35                  40                  45

Gly Val Thr Val Ser Lys Lys Phe Gly Lys Ala His Gln Arg Asn Arg
    50                  55                  60

Phe Lys Arg Ile Val Arg Glu Ala Phe Arg His Val Arg Pro Asn Leu
65                  70                  75                  80

Pro Ala Cys Gln Val Val Val Ser Pro Lys Gly Gly Thr Leu Pro Asn
                85                  90                  95

Phe Gly Lys Leu Ser Ala Asp Leu Leu Lys His Ile Pro Glu Ala Leu
            100                 105                 110

Pro Leu Val Thr Ser Ser Lys
        115

<210> SEQ ID NO 53
<211> LENGTH: 139
<212> TYPE: PRT
<213> ORGANISM: Chlamydophila psittaci

<400> SEQUENCE: 53

Val His Arg Ser Thr Leu Pro Lys Tyr Ala Arg Val Leu Lys Arg Lys
 1               5                  10                  15

Gln Phe Leu Tyr Ile Ser Arg Ala Gly Ser His Cys Gln Gly Ser Gln
            20                  25                  30

Val Ile Phe His Val Ala Pro Ser Arg Tyr Ser Gly Cys Cys Lys Leu
        35                  40                  45

Gly Ile Thr Val Ser Lys Lys Phe Gly Lys Ala His Lys Arg Asn Tyr
    50                  55                  60

Phe Lys Arg Ile Val Arg Glu Ala Phe Arg Lys Lys Arg His Ser Leu
65                  70                  75                  80

Pro Ala Cys Gln Ile Val Val Met Pro Lys Asn Lys Gln Gln Pro Lys
                85                  90                  95

Phe Glu Asp Leu Leu Gln Asp Phe Ala Gln Gln Ile Pro Glu Ala Leu
            100                 105                 110

Ser Ser Lys Leu Ala Lys Asn Lys Pro Thr Thr Gly Val Glu Tyr Ser
        115                 120                 125

Pro Lys Asn Glu Lys Cys Glu Ser Val Leu Pro
    130                 135

<210> SEQ ID NO 54
<211> LENGTH: 118
<212> TYPE: PRT
<213> ORGANISM: Treponema denticola

<400> SEQUENCE: 54

Val Ser Asn Phe Thr Phe Ser Gly Glu Glu Arg Leu Arg Asp Arg Ser
 1               5                  10                  15

Cys Ile Lys Ala Val Phe Gln Lys Gly Leu Lys Leu Ser Leu Asn Gly
            20                  25                  30

Val Ser Leu Leu Ile Leu Pro Asn Gly Leu Glu Tyr Asn Arg Phe Leu
        35                  40                  45

Cys Thr Phe Arg Arg Gly Phe Gly Ser Ala Val Met Arg Asn Arg Ser
    50                  55                  60

Arg Arg Ile Ser Lys Glu Ala Tyr Arg His Ile Lys His Arg Leu Lys
65                  70                  75                  80

Thr Gly Asn Asp Ile Ile Leu Leu Val Phe Ser Glu Lys Asp Ser Tyr
                85                  90                  95
```

-continued

```
Ser Leu Arg Leu Glu Gln Leu Thr Ala Leu Phe Leu Lys Ala Lys Met
            100                 105                 110
Tyr Asn Asp Glu Ala Leu
        115

<210> SEQ ID NO 55
<211> LENGTH: 118
<212> TYPE: PRT
<213> ORGANISM: Enterococcus faecalis

<400> SEQUENCE: 55

Met Lys Lys Ser Tyr Arg Val Lys Lys Glu Lys Glu Phe Gln Gln Val
 1               5                  10                  15

Phe Asn Lys Lys Gln Ser Cys Ala Asn Arg Arg Phe Val Val Tyr Val
            20                  25                  30

Leu Glu Lys Pro Gln Gln Ala His Phe Arg Val Gly Ile Ser Val Gly
         35                  40                  45

Lys Lys Ile Gly Asn Ala Val Thr Arg Asn Ala Val Lys Arg Lys Ile
     50                  55                  60

Arg Ala Ser Leu Phe Gln Leu Lys Asp Arg Ile Ser Pro Glu Ile Asp
 65                  70                  75                  80

Phe Ile Val Ile Ala Arg Pro Gly Leu Glu Lys Leu Ser Ser Glu Glu
                 85                  90                  95

Val Lys Ala Asn Leu Thr His Val Leu Asn Leu Ala Lys Ile Leu Asp
            100                 105                 110

Val Arg Glu Gly Ile Glu
        115

<210> SEQ ID NO 56
<211> LENGTH: 109
<212> TYPE: PRT
<213> ORGANISM: Legionella pneumophila

<400> SEQUENCE: 56

Gln Pro His Arg Leu Leu Lys Lys Asn His Phe Asp Phe Val Phe Gln
 1               5                  10                  15

Ser Ala Lys Lys Ile Pro Thr Asp Asp Phe Ile Phe Leu Phe Arg Glu
            20                  25                  30

Asn Lys Leu Gly Tyr Ala Arg Leu Gly Leu Ala Leu Ser Lys Lys Met
         35                  40                  45

Ile Ala Lys Ala His Asp Arg Asn Arg Ile Lys Arg Leu Leu Arg Glu
     50                  55                  60

Ser Phe Arg His Thr Asn Leu Pro Ala Val Asp Ile Ile Leu Ala
 65                  70                  75                  80

Arg Pro Gly Leu Ala Lys Lys Thr Asn Leu Gly Ile Asn Thr Lys Leu
                 85                  90                  95

Asn Lys Thr Trp Glu Lys Leu Ala Ser Cys Tyr Gly Lys
            100                 105

<210> SEQ ID NO 57
<211> LENGTH: 115
<212> TYPE: PRT
<213> ORGANISM: Staphylococcus epidermis

<400> SEQUENCE: 57

Met Glu Lys Ala Tyr Arg Ile Lys Arg Asn Ser Asp Phe Gln Ala Ile
 1               5                  10                  15

Tyr Lys Asn Gly Lys Ser Val Ala Asn Arg Gln Phe Val Val Tyr Thr
```

-continued

```
            20                  25                  30

Tyr Lys Asn Arg Asp Leu Lys His Phe Arg Leu Gly Ile Ser Val Ser
        35                  40                  45

Lys Lys Leu Gly Asn Ala Val Thr Arg Asn Arg Ile Lys Arg Ala Ile
    50                  55                  60

Arg Glu Asn Phe Lys Val His Lys Gln Asn Ile Ile Ala Lys Asp Ile
65                  70                  75                  80

Ile Val Ile Ala Arg Gln Pro Ala Lys Asp Met Asn Thr Leu Glu Ile
                85                  90                  95

Gln Ser Ser Leu Glu His Val Leu Lys Ile Ala Lys Val Phe Asn Lys
            100                 105                 110

Lys Ile Lys
        115

<210> SEQ ID NO 58
<211> LENGTH: 130
<212> TYPE: PRT
<213> ORGANISM: Mycobacterium smegmatis

<400> SEQUENCE: 58

Val Leu Pro Ala Arg Asn Arg Met Arg Arg Ser Ala Glu Phe Ser Val
 1               5                  10                  15

Thr Val Ser Arg Gly Val Arg Ala Ala Gln Pro Asp Val Val Val His
            20                  25                  30

Ala Leu Arg Leu Glu Ser Asn Ala Gly Asn Ala Gly Asp Asp Gly Asp
        35                  40                  45

Asp Gly Asp Ala Asn Gly Pro Arg Ile Gly Leu Ile Val Ser Lys Ala
    50                  55                  60

Val Gly Asn Ala Val Glu Arg His Arg Val Ser Arg Arg Leu Arg His
65                  70                  75                  80

Val Ala Lys Thr Phe Val Ser Gly Leu Asp Pro Ala Asp Leu Ile Val
                85                  90                  95

Ile Arg Ala Arg Pro Ser Ser Arg Asp Ala Thr Ser Ser Arg Leu Glu
            100                 105                 110

Arg Gln Leu Gly Gln Ala Leu Glu Arg Val Ser Ser Lys Arg Arg Ala
        115                 120                 125

Ser Pro
    130

<210> SEQ ID NO 59
<211> LENGTH: 97
<212> TYPE: PRT
<213> ORGANISM: Burkholderia pseudomallei

<400> SEQUENCE: 59

Val Arg Gly Ser Ile Pro Leu Gln Ala Ser Ala Ala Phe Pro Lys Ala
 1               5                  10                  15

Ala Arg Leu Leu Lys Thr Asp Glu Phe Ser Ser Val Phe Arg Leu Arg
            20                  25                  30

Pro Trp Arg Arg Thr Ala His Phe Val Ile Tyr Gly Lys Pro Thr Gly
        35                  40                  45

Arg Asp Ala Arg Leu Gly Leu Val Ile Gly Lys Lys Tyr Ala Ala Arg
    50                  55                  60

Ala Val Thr Arg Asn Leu Val Lys Arg Leu Ala Arg Glu Ala Phe Arg
65                  70                  75                  80

Thr Arg Arg Ala Glu Phe Ala Gly Trp Asp Ile Leu Leu Arg Leu His
```

```
                    85                  90                  95
Ala

<210> SEQ ID NO 60
<211> LENGTH: 113
<212> TYPE: PRT
<213> ORGANISM: Ureaplasma urealyticum

<400> SEQUENCE: 60

Met Ala Asn Phe Ile Ser Leu Lys Lys Asn Glu Asp Ile Leu Asp Thr
  1               5                  10                  15

Ile Lys Lys Gln Gln Lys Ile His Ser Asn Gln Ile Val Val Tyr Phe
                 20                  25                  30

Arg Lys Thr Asn Leu Lys Asn Val Arg Leu Ala Ile Ser Ile Ser Lys
             35                  40                  45

Lys Lys Phe Lys Leu Ala Thr Gln Arg Asn Arg Ile Arg Arg Leu Ile
         50                  55                  60

Lys Ala Trp Phe Ile Ala Ala Asp Ile Pro Ile Lys Ser Tyr Asp Ile
 65                  70                  75                  80

Val Val Leu Val Lys Pro Ser Phe Ile Asp Gly Ser Phe Val Leu Asn
                 85                  90                  95

Cys Asn Asn Leu Lys Ile Ile Leu Gln Arg Ile Ile Asn Lys Glu Lys
                100                 105                 110

Arg
```